(12) United States Patent
Samaritani et al.

(10) Patent No.: US 8,309,069 B2
(45) Date of Patent: *Nov. 13, 2012

(54) HUMAN SERUM ALBUMIN-FREE STABILIZED INTERFERON LIQUID FORMULATIONS

(75) Inventors: Fabrizio Samaritani, Rome (IT); Alessandra Del Rio, Rome (IT)

(73) Assignee: Ares Trading S.A., Aubonne (CH)

( * ) Notice: Subject to any disclaimer, the term of this patent is extended or adjusted under 35 U.S.C. 154(b) by 1088 days.

This patent is subject to a terminal disclaimer.

(21) Appl. No.: 10/554,602

(22) PCT Filed: Apr. 29, 2004

(86) PCT No.: PCT/EP2004/004806
§ 371 (c)(1), (2), (4) Date: Oct. 16, 2006

(87) PCT Pub. No.: WO2004/096263
PCT Pub. Date: Nov. 11, 2004

(65) Prior Publication Data
US 2007/0059285 A1 Mar. 15, 2007

(30) Foreign Application Priority Data
May 1, 2003 (EP) .................................... 03101210

(51) Int. Cl.
*A61K 38/21* (2006.01)
*A61K 38/00* (2006.01)
*C07K 14/565* (2006.01)

(52) U.S. Cl. .................... 424/85.6; 530/351; 514/1.1

(58) Field of Classification Search .................. None
See application file for complete search history.

(56) References Cited

U.S. PATENT DOCUMENTS

| | | | |
|---|---|---|---|
| 5,762,923 A | 6/1998 | Gross et al. | |
| 5,858,001 A * | 1/1999 | Tsals et al. ..................... | 604/135 |
| 6,569,420 B2 * | 5/2003 | Chen et al. .................... | 424/85.4 |
| 6,923,956 B1 | 8/2005 | Tschope et al. | |
| 2002/0172661 A1 | 11/2002 | Shirley et al. | |
| 2003/0138491 A1 * | 7/2003 | Tracy et al. .................... | 424/486 |
| 2007/0104682 A1 | 5/2007 | Del Curto | |
| 2007/0244299 A1 | 10/2007 | Jaber | |
| 2007/0248674 A1 | 10/2007 | Del Curto et al. | |

FOREIGN PATENT DOCUMENTS

| | | |
|---|---|---|
| EP | 736 303 | 10/1996 |
| EP | 1 250 932 | 10/2002 |
| WO | WO 95/31213 | 11/1995 |
| WO | WO 98/28007 | 7/1998 |
| WO | WO 02/080976 A2 | 10/2002 |

OTHER PUBLICATIONS

Prisms Study Group, "Randomised double-blind placebo-controlled study of interferon β-1a in relapsing/remitting multiple sclerosis", The Lancet, vol. 352, pp. 1498-1504 Nov. 7, 1998.
Andrew Clegg et al., "Immunomodulatory drugs for multiple sclerosis: a systematic review of clinical and cost effectiveness", Exp.Opin. Pharmacother, vol. 2 No. 4, pp. 623-639 2001.
Rik Derynck et al., "Isolation and structure of a human fibroblast interferon gene", Nature, vol. 285, pp. 542-547 Jun. 19, 1980.
Philip C. Familletti, et al., "A convenient and rapid cytopathic effect inhibition assay for interferon", Methods in Enzymology, vol. 78, pp. 387-394 1981.
Catharina Hultgren et al., "The antiviral compound ribavirin modulates the T helper (Th)1/Th2 subset balance in hepatitis B and C virus-specific immune responses", Journal of General Virology, vol. 79, pp. 2381-2391 1998.
Joseph B. McCormick et al., "Lassa Fever effective therapy with ribavirin", The New England Journal of Medicine, vol. 314, No. 1, pp. 20-26 Jan. 2, 1986.
D.F. Mark, et al., "Site-specific mutagenesis of the human fibroblast interferon gene", Proc. Natl. Acad. Sci. USA, vol. 81, pp. 5662-5666 1984.
Sidney Pestka, "Interferon standards and general abbreviations", Methods in Enzymology, vol. 119, 14-23 1986.
Sara Rubinstein, et al., "Convenient assay for interferons", Journal of Virology, vol. 37, No. 2, pp. 755-758 1981.
H. Michael Shepard, et al. "A single amino acid change in IFN-$β_1$ abolishes its antiviral activity", Nature, vol. 294 pp. 563-565 Dec. 10, 1981.
U.S. Appl. No. 12/738,375, filed Apr. 16, 2010, Alessandra Dell Rio.
Japanese Office Action dated Oct. 5, 2010 as received in the corresponding Japanese Application No. 2006-505383.

* cited by examiner

*Primary Examiner* — Robert Landsman
*Assistant Examiner* — Bruce D Hissong
(74) *Attorney, Agent, or Firm* — Woodard Emhardt Moriarty McNett & Henry LLP

(57) ABSTRACT

A stabilized HSA-free liquid pharmaceutical composition is described, which comprises an interferon (IFN), wherein said formulation is a solution that comprises a buffer, a surfactant, an isotonicity agent and an antioxidant. Preferably the interferon is human recombinant IFN-beta.

15 Claims, 13 Drawing Sheets

HUMAN SERUM ALBUMIN-FREE STABILIZED INTERFERON LIQUID FORMULATIONS

FIELD OF THE INVENTION

The invention relates generally to pharmaceutical compositions containing an interferon, more particularly to stabilized formulations of interferon-beta that are free of human serum albumin as an added pharmaceutical excipient.

BACKGROUND OF THE INVENTION

Interferons are cytokines, i.e. soluble proteins that transmit messages between cells and play an essential role in the immune system by helping to destroy microorganisms that cause infection and repairing any resulting damage. Interferons are naturally secreted by infected cells and were first identified in 1957. Their name is derived from the fact that they "interfere" with viral replication and production.

Interferons exhibit both antiviral and antiproliferative activity. On the basis of biochemical and immunological properties, the naturally-occurring human interferons are grouped into three major classes: interferon-alpha (leukocyte), interferon-beta (fibroblast) and interferon-gamma (immune). Alpha-interferon is currently approved in the United States and other countries for the treatment of hairy cell leukemia, venereal warts, Kaposi's Sarcoma (a cancer commonly afflicting patients suffering from Acquired Immune Deficiency Syndrome (AIDS)), and chronic non-A, non-B hepatitis.

Further, interferons (IFNs) are glycoproteins produced by the body in response to a viral infection. They inhibit the multiplication of viruses in protected cells. Consisting of a lower molecular weight protein, IFNs are remarkably non-specific in their action, i.e. IFN induced by one virus is effective against a broad range of other viruses. They are however species-specific, i.e. IFN produced by one species will only stimulate antiviral activity in cells of the same or a closely related species. IFNs were the first group of cytokines to be exploited for their potential anti-tumor and antiviral activities.

The three major IFNs are referred to as IFN-α, IFN-β and IFN-γ. Such main kinds of IFNs were initially classified according to their cells of origin (leukocyte, fibroblast or T cell). However, it became clear that several types might be produced by one cell. Hence leukocyte IFN is now called IFN-α, fibroblast IFN is IFN-β and T cell IFN is IFN-γ. There is also a fourth type of IFN, lymphoblastoid IFN, produced in the "Namalwa" cell line (derived from Burkitt's lymphoma), which seems to produce a mixture of both leukocyte and fibroblast IFN.

The interferon unit or International unit for interferon (U or IU, for international unit) has been reported as a measure of IFN activity defined as the amount necessary to protect 50% of the cells against viral damage. The assay that may be used to measure bioactivity is the cytopathic effect inhibition assay as described (Rubinstein, et al. 1981; Familletti, P. C., et al., 1981). In this antiviral assay for interferon about 1 unit/ml of interferon is the quantity necessary to produce a cytopathic effect of 50%. The units are determined with respect to the international reference standard for Hu-IFN-beta provided by the National Institutes of Health (Pestka, S. 1986).

Every class of IFN contains several distinct types. IFN-β and IFNγ are each the product of a single gene.

The proteins classified as IFNs-α are the most diverse group, containing about 15 types. There is a cluster of IFN-α genes on chromosome 9, containing at least 23 members, of which 15 are active and transcribed. Mature IFNs-α are not glycosylated.

IFNs-α and IFN-β are all the same length (165 or 166 amino acids) with similar biological activities. IFNs-γ are 146 amino acids in length, and resemble the α and β classes less closely. Only IFNs-γ can activate macrophages or induce the maturation of killer T cells. These new types of therapeutic agents can are sometimes called biologic response modifiers (BRMs), because they have an effect on the response of the organism to the tumor, affecting recognition via immunomodulation.

Human fibroblast interferon (IFN-β) has antiviral activity and can also stimulate natural killer cells against neoplastic cells. It is a polypeptide of about 20,000 Da induced by viruses and double-stranded RNAs. From the nucleotide sequence of the gene for fibroblast interferon, cloned by recombinant DNA technology, (Derynk et al. 1980) deduced the complete amino acid sequence of the protein. It is 166 amino acid long.

Shepard et al. (1981) described a mutation at base 842 (Cys→Tyr at position 141) that abolished its anti-viral activity, and a variant clone with a deletion of nucleotides 1119-1121.

Mark et al. (1984) inserted an artificial mutation by replacing base 469 (T) with (A) causing an amino acid switch from Cys→Ser at position 17. The resulting IFN-β was reported to be as active as the 'native' IFN-β and stable during long-term storage (−70° C.).

Rebif® (Serono—recombinant human interferon-β), the latest development in interferon therapy for multiple sclerosis (MS), is interferon(IFN)-beta-1a, produced from mammalian cell lines. Its recommended International Non-proprietary Name (INN) is "Interferon beta-1a".

As with all protein-based pharmaceuticals, one major obstacle that must be overcome in the use of IFN-beta as a therapeutic agent, is the loss of pharmaceutical utility that can result from its instability in pharmaceutical formulations.

Physical instabilities that threaten polypeptide activity and efficacy in pharmaceutical formulations include denaturation and formation of soluble and insoluble aggregates, while chemical instabilities include hydrolysis, imide formation, oxidation, racemization, and deamidation. Some of these changes are known to lead to the loss or reduction of the pharmaceutical activity of the protein of interest. In other cases, the precise effects of these changes are unknown, but the resulting degradative products are still considered to be pharmaceutically unacceptable due to the potential for undesirable side effects.

The stabilization of polypeptides in pharmaceutical compositions remains an area in which trial and error plays a major role (reviewed by Wang (1999) Int. J. Pharm. 185:129-188; Wang and Hanson (1988) J. Parenteral Sci. Tech. 42:S3-S26). Excipients that are added to polypeptide pharmaceutical formulations to increase their stability include buffers, sugars, surfactants, amino acids, polyethylene glycols, and polymers, but the stabilizing effects of these chemical additives vary depending on the protein.

Current IFN-beta formulations employ the use of HSA as a solubility-enhancing agent for IFN-beta. However, the use of HSA has some drawbacks. HSA is a product of human blood and must therefore be harvested from human subjects. While steps are taken to reduce the risk, the use of human blood products such as HSA carries with it the potential introduction of human viruses such as HIV and HCV.

Consequently, there is a need for additional IFN-beta pharmaceutical compositions comprising physiologically compatible stabilizers that improve the solubility of this protein and stabilize the protein against aggregate formation, thereby enhancing their pharmaceutical utility.

DESCRIPTION OF THE INVENTION

The present invention is directed to stabilized pharmaceutical compositions that comprise an interferon (IFN) and methods for their preparation. These compositions are prepared in the absence of human serum albumin (HSA), and are thus free of this pharmaceutical excipient Such compositions are referred to herein as "HSA-free" IFN pharmaceutical compositions and they comprise an interferon (IFN) or an isoform, mutein, fused protein, functional derivative, active fraction or salt thereof, wherein said composition is a solution that comprises a buffer, a surfactant, an isotonicity agent and an antioxidant.

According to an embodiment of the present invention the compositions also comprise a bacteriostatic agent.

An "interferon" or "IFN", as used herein, is intended to include any molecule defined as such in the literature, comprising for example any types of IFNs mentioned in the above section "Background of the Invention". In particular, IFN-α, IFN-β and IFN-γ are included in the above definition. IFN-β is the preferred IFN according to the present invention. IFN-β suitable in accordance with the present invention is commercially available e.g. as Rebif® (Serono), Avonex® (Biogen) or Betaferon® (Schering). The use of interferons of human origin is also preferred in accordance with the present invention. The term interferon, as used herein, is intended to encompass an isoform, a mutein, a fused protein, a functional derivative, an active fraction or a salt thereof.

The term "interferon-beta (IFN-beta or IFN-β)", as used herein, is intended to include fibroblast interferon in particular of human origin, as obtained by isolation from biological fluids or as obtained by DNA recombinant techniques from prokaryotic or eukaryotic host cells, as well as its salts, functional derivatives, variants, analogs and active fragments. Preferably IFN-beta is intended to mean Interferon beta-1a.

As used herein the term "muteins" refers to analogs of IFN in which one or more of the amino acid residues of a natural IFN are replaced by different amino acid residues, or are deleted, or one or more amino acid residues are added to the natural sequence of IFN, without changing considerably the activity of the resulting products as compared to the wild type IFN. These muteins are prepared by known synthesis and/or by site-directed mutagenesis techniques, or any other known technique suitable therefore. Preferred muteins include e.g. the ones described by Shepard et al. (1981) or Mark et al. (1984).

Any such mutein preferably has a sequence of amino acids sufficiently duplicative of that of IFN, such as to have substantially similar or even better activity to an IFN. The biological function of interferon is well known to the person skilled in the art, and biological standards are established and available e.g. from the National Institute for Biological Standards and Control (http://immunology.org/links/NIBSC).

Bioassays for the determination of IFN activity have been described. An IFN assay may for example be carried out as described by Rubinstein et al., 1981. Thus, it can be determined whether any given mutein has substantially a similar, or even a better, activity than IFN by means of routine experimentation.

Muteins of IFN, which can be used in accordance with the present invention, or nucleic acid coding therefor, include a finite set of substantially corresponding sequences as substitution peptides or polynucleotides which can be routinely obtained by one of ordinary skill in the art, without undue experimentation, based on the teachings and guidance presented herein.

Preferred changes for muteins in accordance with the present invention are what are known as "conservative" substitutions. Conservative amino acid substitutions of polypeptides or proteins of the invention, may include synonymous amino acids within a group, which have sufficiently similar physicochemical properties that substitution between members of the group will preserve the biological function of the molecule. It is clear that insertions and deletions of amino acids may also be made in the above-defined sequences without altering their function, particularly if the insertions or deletions only involve a few amino acids, e.g., under thirty, and preferably under ten, and do not remove or displace amino acids which are critical to a functional conformation, e.g., cysteine residues. Proteins and muteins produced by such deletions and/or insertions come within the purview of the present invention.

Preferably, the synonymous amino acid groups are those defined in Table I. More preferably, the synonymous amino acid groups are those defined in Table II; and most preferably the synonymous amino acid groups are those defined in Table III.

TABLE I

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE II

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |

TABLE II-continued

More Preferred Groups of Synonymous Amino Acids

| Amino Acid | Synonymous Group |
|---|---|
| Lys | Lys, Arg |
| Asp | Asp, Asn |
| Glu | Glu, Gln |
| Met | Met, Phe, Ile, Val, Leu |
| Trp | Trp |

TABLE III

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IFN, for use in the present invention include any known method steps, such as presented in U.S. Pat. Nos. 4,959,314, 4,588,585 and 4,737,462, to Mark et al; 5,116,943 to Koths et al., 4,965,195 to Namen et al; 4,879,111 to Chong et al; and 5,017,691 to Lee et al; and lysine substituted proteins presented in U.S. Pat. No. 4,904,584 (Shaw et al). Specific muteins of IFN-beta have been described, for example by Mark et al., 1984.

The term "fused protein" refers to a polypeptide comprising an IFN, or a mutein thereof, fused to another protein, which e.g., has an extended residence time in body fluids. An IFN may thus be fused to another protein, polypeptide or the like, e.g., an immunoglobulin or a fragment thereof.

"Functional derivatives" as used herein cover derivatives of IFN, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity IFN, and do not confer toxic properties on compositions containing it. These derivatives may, for example, include polyethylene glycol side-chains, which may mask antigenic sites and extend the residence of IFN in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

As "active fractions" of IFN, or muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has no significantly reduced activity as compared to the corresponding IFN.

The term "salts" herein refers to both salts of carboxyl groups and to acid addition salts of amino groups of the proteins described above or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salts must retain the biological activity of the proteins (IFN) relevant to the present invention, i.e., the ability to bind to the corresponding receptor and initiate receptor signaling.

In accordance with the present invention, the use of recombinant human IFN-beta and the compounds of the invention is further particularly preferred.

A special kind of interferon variant has been described recently. The so-called "consensus interferons" are non-naturally occurring variants of IFN (U.S. Pat. No. 6,013,253). According to a preferred embodiment of the invention, the compounds of the invention are used in combination with a consensus interferon.

As used herein, human interferon consensus (IFN-con) shall mean a non-naturally-occurring polypeptide, which predominantly includes those amino acid residues that are common to a subset of IFN-alpha's representative of the majority of the naturally-occurring human leukocyte interferon subtype sequences and which includes, at one or more of those positions where there is no amino acid common to all subtypes, an amino acid which predominantly occurs at that position and in no event includes any amino acid residue which is not existent in that position in at least one naturally-occurring subtype. IFN-con encompasses but is not limited to the amino acid sequences designated IFN-con1, IFN-con2 and IFN-con3 which are disclosed in U.S. Pat. Nos. 4,695,623, 4,897,471 and 5,541,293. DNA sequences encoding IFN-con may be produced as described in the above-mentioned patents, or by other standard methods.

In a further preferred embodiment, the fused protein comprises an Ig fusion. The fusion may be direct, or via a short linker peptide which can be as short as 1 to 3 amino acid residues in length or longer, for example, 13 amino acid residues in length. Said linker may be a tripeptide of the sequence E-F-M (Glu-Phe-Met), for example, or a 13-amino acid linker sequence comprising Glu-Phe-Gly-Ala-Gly-Leu-Val-Leu-Gly-Gly-Gln-Phe-Met SEQ ID NO:1) introduced between the sequence of IFN and the immunoglobulin sequence. The resulting fusion protein may have improved properties, such as an extended residence time in body fluids (half-life), increased specific activity, increased expression level, or the purification of the fusion protein is facilitated.

In a further preferred embodiment, IFN is fused to the constant region of an Ig molecule. Preferably, it is fused to heavy chain regions, like the CH2 and CH3 domains of human IgG1, for example. Other isoforms of Ig molecules are also suitable for the generation of fusion proteins according to the present invention, such as isoforms $IgG_2$, $IgG_3$ or $IgG_4$, or other Ig classes, like IgM or IgA, for example. Fusion proteins may be monomeric or multimeric, hetero- or homomultimeric.

In a further preferred embodiment, the functional derivative comprises at least one moiety attached to one or more functional groups, which occur as one or more side chains on the amino acid residues. Preferably, the moiety is a polyethylene (PEG) moiety. PEGylation may be carried out by known methods, such as the ones described in WO99/55377, for example.

The dosage administered, as single or multiple doses, to an individual will vary depending upon a variety of factors, including pharmacokinetic properties, the route of administration, patient conditions and characteristics (sex, age, body weight, health, size), extent of symptoms, concurrent treatments, frequency of treatment and the effect desired.

Standard dosages of human IFN-beta range from 80 000 IU/kg and 200 000 IU/kg per day or 6 MIU (million international units) and 12 MIU per person per day or 22 to 44 µg (microgram) per person. In accordance with the present invention, IFN may preferably be administered at a dosage of about 1 to 50 µg, more preferably of about 10 to 30 µg or about 10 to 20 µg per person per day.

The administration of active ingredients in accordance with the present invention may be by intravenous, intramuscular or subcutaneous route. The preferred route of administration for IFN is the subcutaneous route.

IFN may also be administered daily or every other day, of less frequent. Preferably, IFN is administered one, twice or three times per week.

The preferred route of administration is subcutaneous administration, administered e.g. three times a week. A further preferred route of administration is the intramuscular administration, which may e.g. be applied once a week.

Preferably 22 to 44 µg or 6 MIU to 12 MIU of IFN-beta is administered three times a week by subcutaneous injection.

IFN-beta may be administered subcutaneously, at a dosage of 25 to 30 µg or 8 MIU to 9.6 MIU, every other day. 30 µg or 6 MIU IFN-beta may further be administered intramuscularly once a week.

The term "stability" refers to the physical, chemical, and conformational stability of formulations of interferon of the present invention (including maintenance of biological potency). Instability of a protein formulation may be caused by chemical degradation or aggregation of the protein molecules to form higher order polymers, deglycosylation, modification of glycosylation, oxidation or any other structural modification that reduces at least one biological activity of an interferon polypeptide included in the present invention.

A "stable" solution or formulation, is one wherein the degree of degradation, modification, aggregation, loss of biological activity and the like, of proteins therein is acceptably controlled, and does not increase unacceptably with time. Preferably the formulation retains at least at or about 60%, more preferably at least at or about 70%, most preferably at least at or about 80% of the labelled interferon activity over a period of from 12 to 24 months. The stabilized HSA-free IFN compositions of the invention preferably have a shelf-life of at least about 6 months, 12 months, 18 months, more preferably at least 20 months, still more preferably at least about 22 months, most preferably at least about 24 months when stored at 2-8° C.

Methods for monitoring stability of the HSA-free IFN pharmaceutical compositions of the invention are available in the art, including those methods described in the examples disclosed herein. Thus, IFN aggregate formation during storage of a liquid pharmaceutical composition of the invention can be readily determined by measuring the change in soluble IFN in solution over time. Amount of soluble polypeptide in solution can be quantified by a number of analytical assays adapted to detection of IFN. Such assays include, for example, reverse phase (RP)-HPLC and UV absorption spectroscopy, as described in the Examples below.

Determination of both soluble and insoluble aggregates during storage in liquid formulations can be achieved, for example, using analytical ultracentrifugation as noted in the Examples below to distinguish between that portion of the soluble polypeptide that is present as soluble aggregates and that portion that is present in the nonaggregate, biologically active molecular form.

The expression "multi-dose use" is intended to include the use of a single vial, ampoule or cartridge of an interferon formulation for more than one injection, for example 2, 3, 4, 5, 6 or more injections. The injections are preferably made over a period of at least at or about 12 hours, 24 hours, 48 hours, etc., preferably up to a period of at or about 12 days. The injections may be spaced in time, for example, by a period of 6, 12, 24, 48 or 72 hours.

The term "buffer" or "physiologically-acceptable buffer" refers to solutions of compounds that are known to be safe for pharmaceutical or veterinary use in formulations and that have the effect of maintaining or controlling the pH of the formulation in the pH range desired for the formulation. Acceptable buffers for controlling pH at a moderately acidic pH to a moderately basic pH include, but are not limited to, such compounds as phosphate, acetate, citrate, arginine, TRIS, and histidine. "TRIS" refers to 2-amino-2-hydroxymethyl-1,3, -propanediol, and to any pharmacologically acceptable salt thereof. Preferable buffers are acetate buffers with saline or an acceptable salt.

An "isotonicity agent" is a compound that is physiologically tolerated and imparts a suitable tonicity to a formulation to prevent the net flow of water across cell membranes that are in contact with the formulation. Compounds such as glycerin, are commonly used for such purposes at known concentrations. Other suitable isotonicity agents include, but are not limited to, amino acids or proteins (e.g. glycine or albumin), salts (e.g. sodium chloride), and sugars (e.g. dextrose, mannitol, sucrose and lactose). Preferably the isotonicity agent is mannitol.

The term "antioxidant" refers to a compound that prevents oxygen or oxygen-derived free radicals from interacting with other substances. Antioxidants are among a number of excipients commonly added to pharmaceutical systems to enhance physical and chemical stability. Antioxidants are added to minimize or retard oxidative processes that occur with some drugs or excipients upon exposure to oxygen or in the presence of free radicals. These processes can often be catalyzed by light, temperature, hydrogen on concentration, presence of trace metals or peroxides. Sulfites, bisufites, thiourea, methionine, salts of ethylenediaminetetraacetic acid (EDTA), butylated hydroxytoluene (BHT), and butylated hydroxy anisole (BHA) are frequently used as antioxidants in drugs. Sodium EDTA has been found to enhance the activity of antioxidants by chelating metallic ions that would otherwise catalyze the oxidation reaction. Most preferred antioxidant is methionine.

The term "bacteriostatic" refers to a compound or compositions added to a formulation to act as an anti-bacterial agent. A preserved interferon-containing formulation of the present invention preferably meets statutory or regulatory guidelines for preservative effectiveness to be a commercially viable multi-use product. Examples of bacteriostatics include phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal. Preferably the bacteriostatic agent is benzyl alcohol.

The term "surfactant" refers to a soluble compound that reduces the surface tension of liquids, or reduces interfacial tension between two liquids or a liquid and a solid, the surface tension being the force acting on the surface of a liquid, tending to minimize the area of the surface. Surfactants have sometimes been used in pharmaceutical formulations, including delivery of low molecular mass drugs and polypeptides, in order to modify the absorption of the drug or its delivery to the target tissues. Well known surfactants include polysorbates (Polyoxyethylene derivatives; Tween) as well as Pluronic.

According to a preferred embodiment of the invention, it has been found that by formulating interferon with a surfactant selected from Pluronic® F77, Pluronic F87, Pluronic F88 and Pluronic® F68, particularly preferably Pluronic F68 (BASF, Pluronic F68 is also known as Poloxamer 188) they obtain stable formulations that minimise the loss of active principle caused by adsorption on the surfaces of the vial and/or delivery device (e.g. syringe, pump, catheter, etc.). It has also been found that by formulating interferon with a surfactant selected from Pluronic® F77, Pluronic F87, Pluronic F88 and Pluronic® F68, particularly preferably Pluronic F68 (BASF, Pluronic F68 is also known as Poloxamer 188) they obtain a stable formulation, which is more resistant to oxidation and to formation of proteins aggregates.

The Pluronic surfactants are block copolymers of ethylene oxide (EO) and propylene oxide (PO). The propylene oxide block (PO) is sandwiched between two ethylene oxide (EO) blocks.

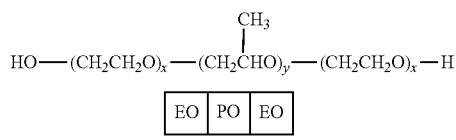

Pluronic surfactants are synthesised in a two-step process:
1. A hydrophobe of the desired molecular weight is created by the controlled addition of propylene oxide to the two hydroxyl groups of propylene glycol; and
2. Ethylene oxide is added to sandwich the hydrophobe between hydrophilic groups. In Pluronic® F77, the percentage of polyoxyethylene (hydrophile) is 70%, and the molecular weight of the hydrophobe (polyoxypropylene) is approximately 2,306 Da.

In Pluronic F87, the percentage of polyoxyethylene (hydrophile) is 70%, and the molecular weight of the hydrophobe (polyoxypropylene) is approximately 2,644 Da.

In Pluronic F88, the percentage of polyoxyethylene (hydrophile) is 80%, and the molecular weight of the hydrophobe (polyoxypropylene) is approximately 2,644 Da.

In Pluronic F68, the percentage of polyoxyethylene (hydrophile) is 80%, and the molecular weight of the hydrophobe (polyoxypropylene) is approximately 1,967 Da.

Typical properties of Pluronic F77 are listed below:
Average Molecular Weight: 6600;
Melt/pour point: 48° C.;
Physical Form @ 20° C.: solid;
Viscosity (Brookfield) cps: 480 [liquids at 25° C., pastes at 60° C. and solids at 77° C.];
Surface tension, dynes/cm @ 25° C.;
   0.1% Conc.: 47.0
   0.01% Conc.: 49.3
   0.001% Conc.: 52.8
Interfacial tension, dynes/cm @ 25° C. vs. Nujol;
   0.1% Conc.: 17.7
   0.01% Conc.: 20.8
   0.01% Conc.: 25.5
Draves Wetting, Seconds 25° C.
   1.0% Conc.: >360
   0.1% Conc.: >360
Foam Height
   Ross Miles, 0.1%, mm @ 50° C.: 100
   Ross Miles, 0.1%, mm @ 26° C.: 47
   Dynamic, 0.1%, mm @ 400 ml/min: >600
Cloud point in aqueous solution, ° C.
   1% Conc.: >100
   10% Conc.: >100
HLB (hydrophile-lipophile balance): 25
   Typical properties of Pluronic F87 are listed below:
Average Molecular Weight: 7700;
Melt/pour point: 49° C.;
Physical Form @ 20° C.: solid;
Viscosity (Brookfield) cps: 700 [liquids at 25° C., pastes at 60° C. and solids at 77° C.];
Surface tension, dynes/cm @ 25° C.;
   0.1% Conc.: 44.0
   0.01% Conc.: 47.0
   0.001% Conc.: 50.2
Interfacial tension, dynes/cm @ 25° C. vs Nujol;
   0.1% Conc.: 17.4
   0.01% Conc.: 20.3
   0.01% Conc.: 23.3
Draves Wetting, Seconds 25° C.
   1.0% Conc.: >360
   0.1% Conc.: >360
Foam Height
   Ross Miles, 0.1%, mm @ 50° C.: 80
   Ross Miles, 0.1%, mm @ 26° C.: 37
   Dynamic, 0.1%, mm @ 400 ml/min: >600
Cloud point in aqueous solution, ° C.
   1% Conc.: >100
   10% Conc.: >100
HLB (hydrophile-lipophile balance): 24
   Typical properties of Pluronic F88 are listed below:
Average Molecular Weight: 11400;
Melt/pour point: 54° C.;
Physical Form @ 20° C.: solid;
Viscosity (Brookfield) cps: 2300 [liquids at 25° C., pastes at 60° C. and solids at 77° C.];
Surface tension, dynes/cm @ 25° C.;
   0.1% Conc.: 48.5
   0.01% Conc.: 52.6
   0.001% Conc.: 55.7
Interfacial tension, dynes/cm @ 25° C. vs Nujol;
   0.1% Conc.: 20.5
   0.01% Conc.: 23.3
   0.01% Conc.: 27.0
Draves Wetting, Seconds 25° C.
   1.0% Conc.: >360
   0.1% Conc.: >360
Foam Height
   Ross Miles, 0.1%, mm @ 50° C.: 80
   Ross Miles, 0.1%, mm @ 26° C.: 37
   Dynamic, 0.1%, mm @ 400 ml/min: >600
Cloud point in aqueous solution, ° C.
   1% Conc.: >100
   10% Conc.: >100
HLB (hydrophile-lipophile balance): 28

Typical properties of Pluronic F68 are listed below:
Average Molecular Weight: 8400;
Melt/pour point: 52° C.;
Physical Form @ 20° C.: solid;
Viscosity (Brookfield) cps: 1000 [liquids at 25° C., pastes at 60° C. and solids at 77° C.];
Surface tension, dynes/cm @ 25° C.;
   0.1% Conc.: 50.3
   0.01% Conc.: 51.2
   0.001% Conc.: 53.6
Interfacial tension, dynes/cm @ 25° C. vs Nujol;
   0.1% Conc.: 19.8
   0.01% Conc.: 24.0
   0.01% Conc.: 26.0
Draves Wetting, Seconds 25° C.
   1.0% Conc.: >360
   0.1% Conc.: >360
Foam Height
   Ross Miles, 0.1%, mm @ 50° C.: 35
   Ross Miles, 0.1%, mm @ 26° C.: 40
   Dynamic, 0.1%, mm @ 400 ml/min: >600
Cloud point in aqueous solution, ° C.
   1% Conc.: >100
   10% Conc.: >100
HLB (hydrophile-lipophile balance): 29

Other polymers having properties similar to those listed above may also be used in the formulations of the invention. The preferred surfactant is Pluronic F68, and surfactants having similar properties.

Pluronic, particularly Pluronic F68, is preferably present at a concentration that is sufficient to maintain interferon stability over the desired storage period (for example 12 to 24 months), and also at a concentration that is sufficient to prevent protein losses due to adsorption on surfaces, such as the vial, ampoule or cartridge or the syringe.

Preferably the concentration of Pluronic, particularly Pluronic F68, in liquid formulations is at or about 0.01 mg/ml to at or about 10 mg/ml, more preferably at or about 0.05 mg/ml to at or about 5 mg/ml, more particularly preferably at or about 0.1 mg/ml to at or about 2 mg/ml, most preferably at or about 1 mg/ml.

Preferably the concentration of IFN-beta in the formulation is at or about 10 µg/ml to at or about 800 µg/ml, more preferably at or about 20 µg/ml to at or about 500 µg/ml, more particularly preferably at or about 30 to at or about 300, most preferably at or about 22, 44, 88 or 264 µg/ml.

Preferably the formulations of the present invention have pH between about 3.0 and at or about 5.0, more preferably at or about 3.7 or 4.7. A preferred buffer is acetate, with preferred counterions being sodium or potassium ions. Acetate saline buffers are well known in the art. Buffer concentrations in total solution can vary between at or about 5 mM, 9.5 mM, 10 mM, 50 mM, 100 mM, 150 mM, 200 mM, 250 mM, and 500 mM. Preferably the buffer concentration is at or about 10 mM. Particularly preferred is a buffer 10 mM in acetate ions with a pH of 3.5±0.2 or 4.5±0.2.

Preferably in the composition of the invention the antioxidant, for example methionine, is present at a concentration of at or about 0.01 to at or about 5.0 mg/ml, more preferably at or about 0.05 to at or about 0.3 mg/ml, most preferably at or about 0.1 mg/ml.

Preferably the concentration of the isotonicity agent (for example mannitol) in liquid formulations is at or about 0.5 mg/ml to at or about 500 mg/ml, more preferably at or about 1 mg/ml to at or about 250 mg/ml, more particularly preferably at or about 10 mg/ml to at or about 100 mg/ml, most preferably at or about 55 mg/ml.

The invention includes liquid formulations. The preferred solvent is water for injection.

Liquid formulations may be mono-dose or multi-dose. Those liquid interferon formulations of the invention that are intended for multi-dose use preferably comprise a bacteriostatic, such as phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal. Particularly preferred are phenol, benzyl alcohol and m-cresol, more preferred is benzyl alcohol. The bacteriostatic agent is used in an amount that will yield a concentration that is effective to maintain the formulation essentially bacteria free (suitable for injection) over the multi-dose injection period, which may be at or about 12 or 24 hours to at or about 12 days, preferably at or about 6 to at or about 12 days. The bacteriostatic is preferably present in a concentration of at or about 0.1% (mass bacteriostatic/mass of solvent) to at or about 2.0%, more preferably at or about 0.2% to at or about 1.0%. In the case of benzyl alcohol, particularly preferred are concentrations of 0.2 or 0.3%). However, the use of a preservative, e.g. benzyl alcohol, is not limited to multi-dose formulations, but may also be added in mono-dose formulations.

The range of interferon in the formulations of the invention includes amounts yielding upon reconstitution, concentrations from about 1.0 µg/ml to about 50 mg/ml, although lower and higher concentrations are operable and are dependent on the intended delivery vehicle, e.g., solution formulations will differ from transdermal patch, pulmonary, transmucosal, or osmotic or micro pump methods. The interferon concentration is preferably at or about 5.0, µg/ml to at or about 2 mg/ml, more preferably at or about 10 µg/ml to at or about 1 µg/ml, most preferably at or about 30 µg/ml to at or about 100 µg/ml.

Preferably the formulations of the invention retain at least at or about 60%, more preferably at least at or about 70%, most preferably at least at or about 80% of the interferon activity at the time of packaging over a period of 24 months.

In a further preferred embodiment, the invention provides a method for manufacturing a liquid pharmaceutical composition as described before.

In yet another preferred embodiment, the invention provides a method for manufacturing a packaged pharmaceutical composition comprising placing a solution comprising the active ingredient and the excipients as described before.

In yet another preferred embodiment, the invention provides an article of manufacture for human pharmaceutical use, comprising a vial comprising the pharmaceutical compositions as described before, and written material stating that such solution may be held over a period of at or about twenty-four hours or greater after the first use. Preferably the written material states that the solution may be held up to at or about 12 days.

After the first use of a multi-dose formulation it may be kept and used for at least at or about 24 hours, preferably at least at or about 4, 5 or 6 days, more preferably for up to 12 days. After the first use the formulation it is preferably stored at below room temperature (i.e. below at or about 25° C.), more preferably below at or about 10° C., more preferably at or about 2-8° C., most preferably at or about 46° C.

The formulations of the present invention can be prepared by a process which comprises adding the calculated amounts of the excipients to the buffered solution and then adding the interferon.

The resulting solution is then placed in vials, ampoules or cartridges. Variations of this process would be recognized by one of ordinary skill in the art. For example, the order the components are added, whether additional additives are used, the temperature and pH at which the formulation is prepared, are all factors that may be optimised for the concentration and means of administration used.

In case of a multi-dose use formulation, the bacteriostatic agent may be added to the solution containing the active ingredient (interferon) or alternatively may be kept in a separate vial or cartridge and subsequently mixed to the solution containing the active ingredient at the moment of use.

The formulations of the invention can be administered using recognized devices. Examples comprising these single vial systems include auto-injector or pen-injector devices for delivery of a solution such as Rebiject®.

The products presently claimed include packaging material. The packaging material provides, in addition to the information required by the regulatory agencies, the conditions under which the product may be used. The packaging material of the present invention provides instructions to the patient, if needed, to prepare the final solution and to use such final solution over a period of twenty-four hours or greater for the two vial, wet/dry, product. For the single vial, solution product, the label indicates that such solution may be used over a period of twenty-four hours or greater. The presently claimed products are useful for human pharmaceutical product use.

The stable preserved formulations may be provided to patients as clear solutions. The solution may be for single use or it may be reused multiple times and may suffice for a single or multiple cycles of patient treatment and thus provides a more convenient treatment regimen than currently available.

The interferon in either the stable or preserved formulations or solutions described herein, may be administered to a patient in accordance with the present invention via a variety of delivery methods including SC or IM injection; transdermal, pulmonary, transmucosal, implant, osmotic pump, cartridge, micro pump, oral, or other means appreciated by the skilled artisan, as well-known in the art.

The term "vial" refers broadly to a reservoir suitable for retaining interferon in solid or liquid form in a contained sterile state. Examples of a vial as used herein include ampoules, cartridges, blister packages, or other such reservoir suitable for delivery of the interferon to the patient via syringe, pump (including osmotic), catheter, transdermal patch, pulmonary or transmucosal spray. Vials suitable for packaging products for parenteral, pulmonary, transmucosal, or transdermal administration are well known and recognized in the art.

The term "treatment" within the context of this invention refers to any beneficial effect on progression of disease, Including attenuation, reduction, decrease or diminishing of the pathological development after onset of disease.

Pharmaceutical compositions of the invention comprising IFN or an isoform, mutein, fused protein, functional derivative, active fraction or salt are useful in the diagnosis, prevention, and treatment (local or systemic) of clinical indications responsive to therapy with this polypeptide. Such clinical indications include, for example, disorders or diseases of the central nervous system (CNS), brain, and/or spinal cord, including multiple sclerosis; autoimmune diseases, including rheumatoid arthritis, psoriasis, Crohn's disease; and cancers, including breast, prostate, bladder, kidney and colon cancers.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning of a range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Example 1

Figure 1:
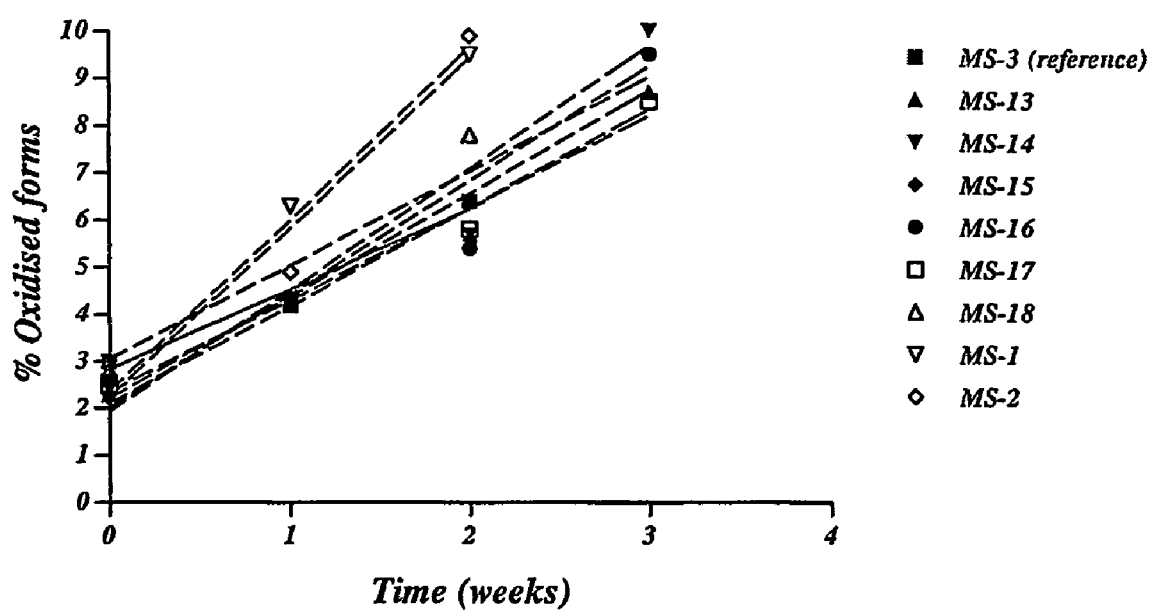
FIG. 1: it reports the percentage of oxidised forms, which are present in Interferon beta-1a multi-dose formulations having different concentrations of benzyl alcohol after storage at 40° C.

Liquid Mono-dose HSA-free Interferon beta-1a Formulation in Pre-filled Syringes 1.1 Preliminary Compatibility Studies Preliminary experiments were conducted to verify the protective effect shown by some excipients like antioxidant and surfactants, since it was expected that the elimination of human serum albumin (HSA) from the current product could have affected the product in terms of oxidation, aggregates formation and adsorption to surfaces.

Interferon beta-1a was formulated at concentrations of 44 mcg/ml and 88 mcg/ml in sodium acetate buffer containing 54.6 mg/ml mannitol in combination with several excipients such as 0.4% HSA, 0.012% L-Methionine, Tween 20 (0.005%, 0.007%, 0.01%), Poloxamer 188 (at 0.05%, 0.1%, 0.5%). The different combinations were exposed to stressing conditions (either storage at 40° C. or vortexing) and tested for oxidation (by RP-HPLC) and aggregation (by SE-HPLC).

Tables DEP-1 and -2 summarize the levels of oxidation and aggregation after 2 weeks of storage at 40° C. The combination of Interferon beta-1a with both surfactants tested (Tween 20 and Poloxamer 188) resulted in an increase in the level of oxidation which, for each type of surfactant, is concentration dependent (Table DEP-1, combinations #4-6 and #7-9); at a level of 0.5% Poloxamer 188 (also mentioned as pluronic F-68 or F-68), the drug substance is completely degraded (Table DEP-1, #9). A higher degradation rate is observed for Tween 20, as expected, due to oxidising species (e.g. peroxides) that can be present as residues from synthesis.

Both surfactants at the different concentrations tested do not influence the level of aggregation upon storage at 40° C. (Table DEP-2).

TABLE DEP-1

Oxidised forms (%) by RP-HPLC after storage at 40° C.

|  |  | T = 0 | 2 w |
|---|---|---|---|
| #1 | IFN 44 | 3.0 | 6.5 |
| #2 | IFN 44 mcg + 0.4% HSA (current | 2.4 | 5.5 |
| #3 | IFN 44 mcg + 0.012% L- | 3.9 | 6.2 |
| #4 | IFN 44 mcg | 3.5 | 6.0 |
| #5 | IFN 44 mcg | 3.4 | 7.0 |
| #6 | IFN 44 mcg | 3.5 | 8.7 |
| #7 | IFN 44 mcg | 3.5 | 6.9 |
| #8 | IFN 44 mcg | 3.3 | 8.0 |
| #9 | IFN 44 mcg | 3.6 | n.m. |
| #10 | IFN 44 mcg + 0.012% L-Met + 0.007% | 3.5 | 6.9 |
| #11 | IFN 44 mcg + 0.012% L- | 3.5 | 7.6 | n.m. = not measurable, since completely

TABLE DEP-2

Total aggregates (%) by SE-HPLC after storage at 40° C.

|  |  | T = 0 | 2 w |
|---|---|---|---|
| #1 | IFN 44 | 2.6 | 2.8 |
| #4 | IFN 44 mcg | 2.4 | 2.1 |
| #5 | IFN 44 mcg | 2.8 | 2.0 |
| #6 | IFN 44 mcg | 2.6 | 2.0 |
| #7 | IFN 44 mcg | 2.5 | 2.9 |
| #8 | IFN 44 mcg | 2.5 | 2.5 |
| #9 | IFN 44 mcg | 2.6 | 2.9 |

Table DEP-3 shows that both surfactants, Tween 20 and Poloxamer 188 (F-68), used at their Critical Micellar Concentration (CMC), help in preventing aggregation induced by 5 min vortexing.

TABLE DEP-3

Total aggregates (%) by SE-HPLC after 5 min vortexing

|  |  | T = 0 | 5' vortex |
|---|---|---|---|
| #1 | IFN 44 mcg | 1.6 | 2.5 |
| #3 | IFN 44 mcg + 0.012%L-Met | 1.4 | 2.4 |
| #10 | IFN 44 mcg + 0.012%L-Met + 0.007% Tween 20 | 1.4 | 1.3 |
| #11 | IFN 44 mcg + 0.012%L-Met + 0.1% F-68 | 1.3 | 1.3 |

1.1.1 Physico-chemical Characteristics

The physico-chemical characteristics that are known to be critical for the quality of the drug product are the amount of oxidation and of dimers/aggregates. These characteristics have been considered in the compatibility studies, summarized above.

1.2 Excipients 1.2.1 10 mM Sodium Acetate Buffer, pH 3.5

A 10 mM sodium acetate buffer at pH 3.5 containing 54.6 mg/ml mannitol as isotonicity agent stabilizes the product, as shown during previous development for the currently marketed product (Rebif®) and as described in EP 759,775.

1.2.2 Poloxamer 188

Poloxamer 188 (or Pluronic F-68) is included in the formulation at a level of 0.1% (Critical Micellar Concentration) in order to prevent adsorption of the drug substance by the surface of the containers during the manufacturing process; higher concentrations may negatively affect the stability of the product (higher oxidation); lower concentrations may be less effective in limiting adsorption.

The effectiveness of Poloxamer 188 to prevent adsorption of the drug substance during the manufacturing process was demonstrated by the following study: solutions containing 44 mcg/ml Interferon beta-1a were combined with 3 different concentrations of a surfactant (Tween 20 or Poloxamer 188) or HSA, mimicking the manufacturing process; samples were taken at different steps (compounding, aseptic filtration, filling) and tested by a quantitative RP-HPLC method.

The following samples were taken:
before filtration (BF)
after $1^{st}$ filtration (AF1)
after $2^{nd}$ filtration (AF2)
after filling (finished product at T=0)

The results are reported in Table DEP4 and are expressed as recovery (%) versus the initial value (i.e. compounded solution before filtration): Poloxamer 188 is more effective than Tween 20, but as effective as HSA in preventing the adsorption of the drug substance during manufacturing.

TABLE DEP-4

% Interferon beta-1a recovery during manufacturing

|  | no HSA/ no surfactant | HSA | 0.003% Tween 20 | 0.007% Tween 20 | 0.02% Tween 20 | 0.05% F-68 | 0.1% F-68 | 0.2% F-68 |
| --- | --- | --- | --- | --- | --- | --- | --- | --- |
| AF1 | 97.8 | 97.5 | 98.2 | 97.7 | 99.1 | 98.3 | 98.6 | 98.9 |
| AF2 | 94.5 | 97.3 | 96.3 | 96.6 | 97.6 | 97.0 | 98.4 | 98.3 |
| T = 0 | 93.8 | 96.9 | 95.8 | 95.7 | 96.3 | 96.5 | 97.0 | 98.0 |

Different grades of Poloxamer 188 obtained from different suppliers were investigated in terms of oxidation products upon accelerated conditions (2 weeks at 40° C.) to define the quality to be used: Poloxamer 188 from BASF was chosen since it provided a lower level of oxidation and it is supplied as pharmaceutical grade. Results are summarized in Table DEP-5:

TABLE DEP-5

% Oxidised forms detected in formulations containing 0.1% Poloxamer 188 (different quality and supplier)

| Supplier | Quality | T = 0 | 1 week at 40° C. | 2 weeks at 40° C. |
| --- | --- | --- | --- | --- |
| BASF | Pharm. Grade | 2.6 | — | 3.2 |
| Fluka | For GC | — | 3.8 | 4.7 |
| Sigma | For biochemistry | — | 3.2 | 4.4 |

1.2.3 L-Methionine

L-Methionine (L-Met) is included in the formulation at a level of 0.012% to limit oxidation. The effectiveness of this concentration is shown by the comparison with a formulation which does not contain L-Methionine; higher concentrations (0.05%, 0.1%) of L-Methionine show a comparable effect on stability. The oxidation products detected upon storage at 400° C. are shown in Table DEP6.

TABLE DEP-6

% Oxidised forms in Interferon beta-1a formulations containing different levels of L-Methionine (L-Met)

|  | T = 0 | 1 week at 40° C. | 4 weeks at 40° C. |
| --- | --- | --- | --- |
| IFNβ-1a 44 mcg | 2.8 | 3.8 | 7.6 |
| IFNβ-1a 44 mcg + 0.012% L-Met | — | 2.9 | 5.3 |
| IFNβ-1a 44 mcg + 0.05% L-Met | — | 3.0 | 5.1 |
| IFNβ-1a 44 mcg + 0.1% L-Met | — | 2.6 | 5.0 |

Figure 12:
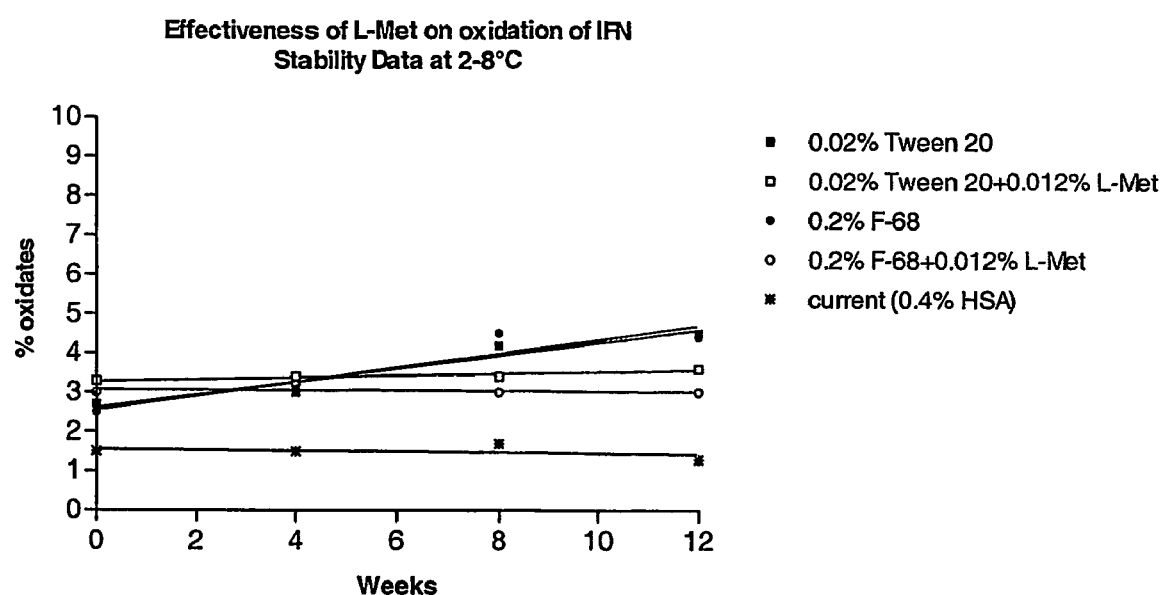
FIG. 12: it shows the effectiveness of 0.012% L-Methionine as antioxidant (at 2-8° C.)
Figure 13:
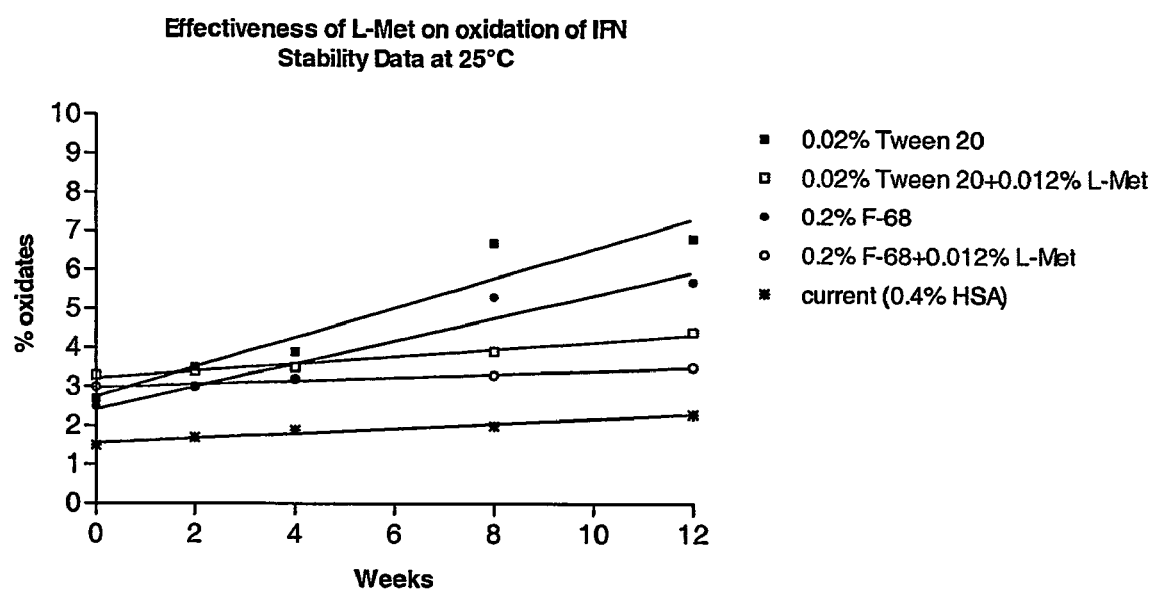
FIG. 13: it shows the effectiveness of 0.012% L-Methionine as antioxidant (at 25±2° C.)

During the formulation development, the effectiveness of L-Methionine as an antioxidant was confirmed by 3 months stability data at 2-8° C. and 25±2° C., generated on formulations with L-Methionine in combination to surfactants: L-Methionine is effective as an antioxidant at a level of 0.012% and can guarantee a stability comparable to the one observed for the current product (see FIGS. 12 and 13).

1.3 Drug Product

1.3.1 Formulation Development

The development of the new HSA-free formulation of Interferon beta-1 a focused on confirmation of the results of the preliminary investigations (effectiveness of L-methionine as antioxidant, inclusion of Poloxamer 188 to prevent losses during manufacturing) in the final container.

Solutions of Interferon beta-1a at 44 mcg/ml and 88 mcg/ml containing 54.6 mg/ml mannitol in 10 mM sodium acetate buffer at pH 3.5 were prepared and the following excipients included:

Tween 20 (0.003%, 0.007%, 0.02%)

Poloxamer 188 (0.05%, 0.1%, 0.2%)

L-Methionine (0%, 0.012%)

HSA (0.4%, current formulation, designated as "ref")

The composition of the formulations that were investigated is shown in Table DEP-7.

TABLE DEP-7

Composition of formulations containing Interferon beta-1a

| Formulation | IFN-β-1a (mcg) | Mannitol (mg) | Tween 20 (mg) | Poloxamer 188 (mg) | HSA (mg) | L-Methionine (mg) | 10 mM Acetate buffer pH 3.5 |
| --- | --- | --- | --- | --- | --- | --- | --- |
| IFN-1 | 44 | 54.6 | 0.03 | — | — | — | q.s. to 1 ml |
| IFN-2 | 44 | 54.6 | 0.07 | — | — | — | q.s. to 1 ml |
| IFN-3 | 44 | 54.6 | 0.2 | — | — | — | q.s. to 1 ml |
| IFN-4 | 44 | 54.6 | — | 0.5 | — | — | q.s. to 1 ml |
| IFN-5 | 44 | 54.6 | — | 1 | — | — | q.s. to 1 ml |
| IFN-6 | 44 | 54.6 | — | 2 | — | — | q.s. to 1 ml |
| IFN-7 (ref) | 44 | 54.6 | — | — | 4 | — | q.s. to 1 ml |
| IFN-8 | 44 | 54.6 | — | — | — | — | q.s. to 1 ml |
| IFN-9 | 44 | 54.6 | 0.2 | — | — | 0.12 | q.s. to 1 ml |
| IFN-10 | 44 | 54.6 | — | 2 | — | 0.12 | q.s. to 1 ml |
| IFN-11 | 88 | 54.6 | — | 1 | — | 0.12 | q.s. to 1 ml |

The formulations were manufactured according to the procedure described below:

90 ml of each formulation were manufactured under aseptic conditions, by compounding the required amount of excipients dissolved in WFI with the drug substance (Interferon beta-1a); the formulations were then filtered through a 0.22 μm membrane (filtered twice through two membrane filters) and 0.5 ml of each solution filled into 1 ml Hypak glass syringes. The batch size was of about 180 syringes.

The formulations were then stored at 2-8° C., 25±2° C. and 40±2° C., and tested for stability up to 12 weeks (up to 6 weeks for samples stored at 40±2° C.).

The following analytical tests and methods were used during the development (for more details on these assays see Example 2):
bioactivity (CPE bioassay)
assay (RP-HPLC method)
oxidation products (RP-HPLC method)
dimers/aggregates (SE-HPLC method and SDS-PAGE)
pH (potentiometric method)
osmolality (crioscopic measurement)

The results and their evaluation are summarized in Tables DEP-8 to DEP-17.

TABLE DEP-8

| Bioidentity (MIU/ml) | | | | |
|---|---|---|---|---|
| 2-8° C. | | | | |
| | 0 Time | 4 weeks | 8 weeks | 12 weeks |
| IFN-1 | 11.7 | 12.4 | 11.6 | 11.0 |
| IFN-2 | 11.5 | 12.1 | 11.9 | 11.1 |
| IFN-3 | 11.3 | 10.0 | 9.9 | 9.7 |
| IFN-4 | 11.8 | 11.8 | 12.4 | 11.1 |
| IFN-5 | 12.1 | 12.3 | 12.6 | 11.6 |
| IFN-6 | 12.1 | 12.2 | 11.4 | 10.7 |
| IFN-7 | 12.1 | 12.4 | 12.6 | 11.1 |
| IFN-8 | 11.2 | 11.4 | 11.5 | 10.8 |
| IFN-9 | 11.2 | 12.4 | 12.7 | 11.9 |
| IFN-10 | 12.0 | 13.0 | 12.4 | 11.6 |
| 25° C. | | | | | |
| | 0 Time | 2 weeks | 4 weeks | 8 weeks | 12 weeks |
| IFN-1 | 11.7 | 11.2 | 11.5 | 11.0 | 10.7 |
| IFN-2 | 11.5 | 11.8 | 11.3 | 11.1 | 10.7 |
| IFN-3 | 11.3 | 10.7 | 10.6 | 10.4 | 8.9 |
| IFN-4 | 11.8 | 10.8 | 11.8 | 12.2 | 11.6 |
| IFN-5 | 12.1 | 12.3 | 12.5 | 12.0 | 10.9 |
| IFN-6 | 12.1 | 12.9 | 12.0 | 11.5 | 10.5 |
| IFN-7 | 12.1 | 11.2 | 12.7 | 12.8 | 11.3 |
| IFN-8 | 11.2 | 11.1 | 11.5 | 11.6 | 10.9 |
| IFN-9 | 11.2 | 11.0 | 12.1 | 11.5 | 10.9 |
| IFN-10 | 12.0 | 11.7 | 11.8 | 12.5 | 11.6 |
| 40° C. | | | | |
| | 0 Time | 2 weeks | 4 weeks | 6 weeks |
| IFN-1 | 11.7 | 9.4 | 9.4 | 9.6 |
| IFN-2 | 11.5 | 10.0 | 9.7 | 9.6 |
| IFN-3 | 11.3 | 7.8 | 7.2 | 6.0 |
| IFN-4 | 11.8 | 10.9 | 11.4 | 13.0 |
| IFN-5 | 12.1 | 12.1 | 13.1 | 12.1 |
| IFN-6 | 12.1 | 11.6 | 12.7 | 11.4 |
| IFN-7 | 12.1 | 11.0 | 12.2 | 12.0 |
| IFN-8 | 11.2 | 11.0 | 11.6 | 12.0 |
| IFN-9 | 11.2 | 10.1 | 9.1 | 7.1 |
| IFN-10 | 12.0 | 12.3 | 12.0 | 11.0 |

The slopes calculated by linear regression analysis and summarized in Table DEP-9 show a decrease in the biological activity for all the formulations containing Tween 20 (#1, 2, 3, 9) and stored at 40° C.; a decrease in the bioactivity is also observed for formulations #3 and 6 (highest concentration of surfactants) after storage at 25° C. and 2-8° C.

TABLE DEP-9

| Linear regression analysis for bioidentity (slopes expressed as MIU/ml × week) | | | | | | | | | | |
|---|---|---|---|---|---|---|---|---|---|---|
| | IFN-1 | IFN-2 | IFN-3 | IFN-4 | IFN-5 | IFN-6 | IFN-7 | IFN-8 | IFN-9 | IFN-10 |
| 2-8° C. | −0.07 | −0.04 | −0.12 | −0.04 | −0.03 | −0.13 | −0.06 | −0.03 | 0.06 | −0.06 |
| 25° C. | −0.08 | −0.08 | −0.17 | 0.03 | −0.10 | −0.17 | −0.02 | −0.01 | −0.02 | 0.00 |
| 40° C. | −0.32 | −0.29 | −0.83 | 0.20 | 0.05 | −0.05 | 0.06 | 0.16 | −0.67 | −0.17 |

TABLE DEP-10

| Assay (mcg/syringe) by RP-HPLC | | | | |
|---|---|---|---|---|
| 2-8° C. | | | | |
| | 0 Time | 4 weeks | 8 weeks | 12 weeks |
| IFN-1 | 23.4 | 21.5 | 22.8 | 21.2 |
| IFN-2 | 22.9 | 21.4 | 22.2 | 21.1 |
| IFN-3 | 22.4 | 20.8 | 20.8 | 20.2 |
| IFN-4 | 22.9 | 22.4 | 23.1 | 21.2 |
| IFN-5 | 23.6 | 23.3 | 21.7 | 22.2 |
| IFN-6 | 23.1 | 21.4 | 22.9 | 21.2 |
| IFN-7 | 23.0 | 22.8 | 23.4 | 22.0 |
| IFN-8 | 21.2 | 20.0 | 23.5 | 20.0 |
| IFN-9 | 23.0 | 21.7 | 21.6 | 22.1 |
| IFN-10 | 22.8 | 22.6 | 22.7 | 23.2 |
| IFN-11 | 45.6 | 43.9 | 44.3 | 44.7 |
| 25° C. | | | | | |
| | 0 Time | 2 weeks | 4 weeks | 8 weeks | 12 weeks |
| IFN-1 | 23.4 | 20.5 | 20.7 | 20.7 | 20.1 |
| IFN-2 | 22.9 | 21.2 | 19.8 | 20.8 | 19.7 |
| IFN-3 | 22.4 | 19.9 | 19.1 | 17.6 | 16.6 |
| IFN-4 | 22.9 | 21.5 | 22.2 | 22.5 | 21.1 |
| IFN-5 | 23.6 | 23.4 | 23.0 | 23.6 | 21.4 |
| IFN-6 | 23.1 | 22.6 | 20.7 | 22.0 | 20.5 |
| IFN-7 | 23.0 | 23.1 | 22.9 | 23.2 | 22.6 |
| IFN-8 | 21.2 | 20.8 | 19.8 | 20.8 | 19.7 |
| IFN-9 | 23.0 | 20.5 | 20.2 | 18.2 | 18.6 |
| IFN-10 | 22.8 | 22.2 | 22.6 | 22.0 | 22.3 |
| IFN-11 | 45.6 | 45.2 | 44.6 | 43.4 | 44.8 |
| 40° C. | | | | |
| | 0 Time | 2 weeks | 4 weeks | 6 weeks |
| IFN-1 | 23.4 | 18.8 | 17.8 | 16.6 |
| IFN-2 | 22.9 | 18.5 | 16.2 | 15.4 |
| IFN-3 | 22.4 | 15.1 | 11.2 | 10.4 |
| IFN-4 | 22.9 | 20.1 | 19.8 | 18.7 |
| IFN-5 | 23.6 | 21.8 | 21.0 | 19.6 |
| IFN-6 | 23.1 | 20.7 | 18.8 | 18.7 |
| IFN-7 | 23.0 | 20.6 | 18.8 | 16.7 |

TABLE DEP-10-continued

| Assay (mcg/syringe) by RP-HPLC | | | | |
|---|---|---|---|---|
| IFN-8 | 21.2 | 19.6 | 18.3 | 18.1 |
| IFN-9 | 23.0 | 16.8 | 12.7 | 13.1 |
| IFN-10 | 22.8 | 20.5 | 19.8 | 19.9 |
| IFN-11 | 45.6 | 43.4 | 41.5 | 40.1 |

The slopes calculated by linear regression analysis and summarized in Table DEP-11 show a higher loss in protein content for formulations containing Tween 20 (#1, 2, 3, 9) stored at 40° C.; the same trend is observed at 25° C. as well as for formulations #5 and 6. A significant decrease in protein content occurs at 2-8° C. for formulations #1, 2, 3 (with Tween 20), 4, 5 (with Poloxamer 188) and 9 (with Tween 20 and L-Methionine).

TABLE DEP-11

| Linear regression analysis for the assay (slopes expressed as mcg/syringe × week) | | | | | | | | | | | |
|---|---|---|---|---|---|---|---|---|---|---|---|
| | IFN-1 | IFN-2 | IFN-3 | IFN.4 | IFN-5 | IFN-6 | IFN-7 | IFN-8 | IFN-9 | IFN-10 | IFN-11 |
| 2-8° C. | −0.13 | −0.11 | −0.16 | −0.11 | −0.14 | −0.11 | −0.06 | 0.00 | −0.07 | 0.03 | −0.06 |
| 25° C. | −0.19 | −0.20 | −0.44 | −0.09 | −0.15 | −0.18 | −0.03 | −0.09 | −0.34 | −0.04 | −0.10 |
| 40° C. | −1.10 | −1.20 | −2.00 | −0.64 | −0.64 | −0.76 | −1.00 | −0.53 | −1.70 | −0.47 | −0.92 |

TABLE DEP-12

| % Oxidised forms by RP-HPLC | | | | |
|---|---|---|---|---|
| 2-8° C. | | | | |
| | 0 Time | 4 weeks | 8 weeks | 12 weeks |
| IFN-1 | 2.8 | 2.8 | 3.3 | 3.4 |
| IFN-2 | 2.5 | 2.9 | 3.4 | 3.4 |
| IFN-3 | 2.7 | 3.0 | 4.2 | 4.5 |
| IFN-4 | 2.6 | 2.6 | 3.6 | 3.2 |
| IFN-5 | 2.8 | 2.8 | 3.6 | 3.2 |
| IFN-6 | 2.5 | 3.1 | 4.5 | 4.4 |
| IFN-7 | 1.5 | 1.5 | 1.7 | 1.3 |
| IFN-8 | 2.8 | 2.9 | 3.2 | 3.1 |
| IFN-9 | 3.3 | 3.4 | 3.4 | 3.6 |
| IFN-10 | 3.0 | 3.2 | 3.0 | 3.0 |
| IFN-11 | 2.6 | 2.9 | 2.9 | 2.9 |
| 25° C. | | | | |
| | 0 Time | 2 weeks | 4 weeks | 8 weeks | 12 weeks |
| IFN-1 | 2.8 | 3.0 | 3.1 | 4.2 | 4.3 |
| IFN-2 | 2.5 | 3.0 | 3.1 | 3.4 | 4.6 |
| IFN-3 | 2.7 | 3.5 | 3.9 | 6.7 | 6.8 |
| IFN-4 | 2.6 | 3.0 | 3.1 | 4.7 | 4.8 |
| IFN-5 | 2.8 | 3.0 | 3.1 | 4.4 | 4.5 |
| IFN-6 | 2.5 | 3.0 | 3.2 | 5.3 | 5.7 |
| IFN-7 | 1.5 | 1.7 | 1.9 | 2.0 | 2.3 |
| IFN-8 | 2.8 | 3.1 | 2.9 | 4.1 | 4.3 |
| IFN-9 | 3.3 | 3.4 | 3.5 | 3.9 | 4.4 |
| IFN-10 | 3.0 | 3.0 | 3.2 | 3.3 | 3.5 |
| IFN-11 | 2.6 | 2.8 | 3.1 | 3.2 | 3.4 |
| 40° C. | | | | |
| | 0 Time | 2 weeks | 4 weeks | 6 weeks |
| IFN-1 | 2.8 | 6.0 | 8.3 | 12.4 |
| IFN-2 | 2.5 | 3.7 | 8.7 | 10.7 |
| IFN-3 | 2.7 | 8.8 | 12.3 | 16.9 |
| IFN-4 | 2.6 | 4.1 | 6.7 | 10.3 |
| IFN-5 | 2.8 | 3.7 | 7.2 | 9.6 |
| IFN-6 | 2.5 | 4.9 | 7.6 | 13.3 |
| IFN-7 | 1.5 | 2.8 | 3.9 | 11.8 |
| IFN-8 | 2.8 | 3.8 | 7.6 | 10.7 |
| IFN-9 | 3.3 | 5.7 | 8.6 | 12.8 |
| IFN-10 | 3.0 | 3.6 | 9.3 | 9.7 |
| IFN-11 | 2.6 | 3.2 | 5.3 | 6.8 |

The slopes calculated by linear regression analysis and summarized in Table DEP-13 show that formulations containing Tween 20 have a faster oxidation rate when compared to formulations containing Poloxamer 188 and a level of oxidation dependent on the concentration of Tween 20.

The effectiveness of L-Methionine in limiting oxidation at the different temperatures tested is also shown by comparison of formulation #9 (Tween 20+L-Methionine) with #3 (Tween 20) and formulation #10 (Poloxamer 188+L-Methionine) with #6 (Poloxamer 188).

TABLE DEP-13

Linear regression analysis for the oxidised forms (slopes expressed as % oxidised forms/week)

| | IFN-1 | IFN-2 | IFN-3 | IFN-4 | IFN-5 | IFN-6 | IFN-7 | IFN-8 | IFN-9 | IFN-10 | IFN-11 |
|---|---|---|---|---|---|---|---|---|---|---|---|
| 2-8° C. | 0.06 | 0.08 | 0.17 | 0.07 | 0.05 | 0.17 | −0.01 | 0.03 | 0.02 | 0.00 | 0.02 |
| 25° C. | 0.14 | 0.16 | 0.38 | 0.21 | 0.16 | 0.29 | 0.06 | 0.14 | 0.09 | 0.04 | 0.06 |
| 40° C. | 1.60 | 1.50 | 2.30 | 1.30 | 1.20 | 1.80 | 1.60 | 1.40 | 1.60 | 1.30 | 0.74 |

TABLE DEP-14

Total aggregates (%) by SE-HPLC or SDS-PAGE 2-8° C.

| | 0 Time | 4 weeks | 8 weeks | 12 weeks |
|---|---|---|---|---|
| IFN-1 | 0.8 | 0.5 | 0.7 | 0.5 |
| IFN-2 | 0.8 | 0.4 | 0.7 | 0.3 |
| IFN-3 | 1.1 | 0.6 | 0.9 | 1.2 |
| IFN-4 | 1.2 | 0.9 | 1.4 | 1.7 |
| IFN-5 | 1.0 | 1.4 | 0.9 | 1.6 |
| IFN-6 | 1.1 | 1.8 | 0.9 | 1.5 |
| IFN-7* | ≦3% | <3% | <3% | <4.5% |
| IFN-8 | 1.2 | 1.6 | 1.2 | 2.0 |
| IFN-9 | 1.7 | 1.4 | 1.7 | 1.2 |
| IFN-10 | 1.4 | 1.3 | 1.3 | 1.3 |
| IFN-11 | 1.4 | 0.9 | 0.4 | 1.7 |

25° C.

| | 0 Time | 2 weeks | 4 weeks | 8 weeks | 12 weeks |
|---|---|---|---|---|---|
| IFN-1 | 0.8 | 0.4 | 0.2 | 0.2 | 0.3 |
| IFN-2 | 0.8 | 0.4 | 0.1 | 0.3 | 0.0 |
| IFN-3 | 1.1 | 0.6 | 0.3 | 0.3 | 0.5 |
| IFN-4 | 1.2 | 1.2 | 0.6 | 0.9 | 0.9 |
| IFN-5 | 1.0 | 0.6 | 0.8 | 0.4 | 0.9 |
| IFN-6 | 1.1 | 0.7 | 0.9 | 0.6 | 0.8 |
| IFN-7* | ≦3% | <3% | <3% | <3% | <4.5% |
| IFN-8 | 1.2 | 0.8 | 0.9 | 0.4 | 0.9 |
| IFN-9 | 1.7 | 0.6 | 0.9 | 0.6 | 0.5 |
| IFN-10 | 1.4 | 0.5 | 0.7 | 0.5 | 0.5 |
| IFN-11 | 1.4 | 1.1 | 0.9 | 0.5 | 1.4 |

40° C.

| | 0 Time | 2 weeks | 4 weeks | 6 weeks |
|---|---|---|---|---|
| IFN-1 | 0.8 | 0.5 | 0.4 | 0.9 |
| IFN-2 | 0.8 | 0.6 | 0.6 | 0.8 |
| IFN-3 | 1.1 | 0.7 | 0.5 | 0.6 |
| IFN-4 | 1.2 | 1.4 | 0.6 | 1.1 |
| IFN-5 | 1.0 | 0.9 | 1.1 | 1.4 |
| IFN-6 | 1.1 | 1.1 | 1.2 | 1.4 |
| IFN-7* | ≦3% | <3% | ≦3% | <4.5% |
| IFN-8 | 1.2 | 0.8 | 0.7 | 0.6 |
| IFN-9 | 1.7 | 0.8 | 1.0 | 0.6 |
| IFN-10 | 1.4 | 0.8 | 1.4 | 1.0 |
| IFN-11 | 1.4 | 1.3 | 1.2 | 1.8 |

*by SDS-PAGE

The slopes calculated by linear regression analysis and summarized in Table DEP-15 show that no significant increase in total aggregates content occurs upon storage at the different temperatures.

TABLE DEP-15

Linear regression analysis for total aggregates (slopes expressed as % total aggregates/week)

|  | IFN-1 | IFN-2 | IFN-3 | IFN-4 | IFN-5 | IFN-6 | IFN-8 | IFN-9 | IFN-10 | IFN-11 |
|---|---|---|---|---|---|---|---|---|---|---|
| 2-8° C. | −0.01 | −0.03 | 0.01 | 0.04 | 0.04 | 0.01 | 0.05 | −0.03 | −0.01 | 0.01 |
| 25° C. | −0.04 | −0.05 | −0.04 | −0.03 | −0.01 | −0.03 | −0.03 | −0.07 | −0.05 | −0.01 |
| 40° C. | 0.01 | 0.01 | −0.09 | −0.07 | 0.07 | 0.05 | −0.10 | −0.15 | −0.03 | 0.07 |

TABLE DEP-16 pH values at 2-8° C.

2-8° C.

|  | 0 Time | 4 weeks | 8 weeks | 12 weeks | 24 weeks | 104 weeks |
|---|---|---|---|---|---|---|
| IFN-1 | 3.7 | 3.7 | 3.7 | 3.7 | — | — |
| IFN-2 | 3.7 | 3.7 | 3.7 | 3.7 | — | — |
| IFN-3 | 3.7 | 3.7 | 3.6 | 3.6 | — | — |
| IFN-4 | 3.7 | 3.8 | 3.7 | 3.6 | — | — |
| IFN-5 | 3.7 | 3.7 | 3.7 | 3.7 | — | — |
| IFN-6 | 3.6 | 3.7 | 3.7 | 3.7 | — | 3.7 |
| IFN-7 | 3.6 | 3.5 | 3.6 | 3.6 | — | 3.6 |
| IFN-8 | 3.6 | 3.6 | 3.7 | 3.7 | — | 3.7 |
| IFN-9 | 3.6 | 3.7 | 3.6 | 3.7 | — | — |
| IFN-10 | 3.6 | 3.7 | 3.7 | 3.7 | — | 3.7 |
| IFN-11 | 3.5 | 3.6 | 3.6 | 3.6 | 3.6 | — |

25° C.

|  | 0 Time | 2 weeks | 4 weeks | 8 weeks | 12 weeks | 24 weeks |
|---|---|---|---|---|---|---|
| IFN-1 | 3.7 | 3.6 | 3.8 | 3.6 | 3.7 | — |
| IFN-2 | 3.7 | 3.6 | 3.8 | 3.6 | 3.7 | — |
| IFN-3 | 3.7 | 3.6 | 3.8 | 3.7 | 3.7 | — |
| IFN-4 | 3.7 | 3.6 | 3.8 | 3.7 | 3.7 | — |
| IFN-5 | 3.7 | 3.7 | 3.6 | 3.7 | 3.7 | — |
| IFN-6 | 3.6 | 3.7 | 3.7 | 3.6 | 3.7 | — |
| IFN-7 | 3.6 | 3.6 | 3.5 | 3.6 | 3.6 | — |
| IFN-8 | 3.6 | 3.7 | 3.6 | 3.7 | 3.7 | — |
| IFN-9 | 3.6 | 3.7 | 3.7 | 3.6 | 3.6 | — |
| IFN-10 | 3.6 | 3.7 | 3.7 | 3.7 | 3.6 | — |
| IFN-11 | 3.5 | 3.6 | 3.6 | 3.6 | 3.6 | 3.6 |

40° C.

|  | 0 Time | 2 weeks | 4 weeks | 6 weeks |
|---|---|---|---|---|
| IFN-1 | 3.7 | 3.6 | 3.7 | 3.7 |
| IFN-2 | 3.7 | 3.6 | 3.7 | 3.8 |
| IFN-3 | 3.7 | 3.6 | 3.7 | 3.8 |
| IFN-4 | 3.7 | 3.6 | 3.7 | 3.8 |
| IFN-5 | 3.7 | 3.7 | 3.6 | 3.7 |
| IFN-6 | 3.6 | 3.7 | 3.6 | 4.0 |
| IFN-7 | 3.6 | 3.6 | 3.6 | 3.6 |
| IFN-8 | 3.6 | 3.6 | 3.7 | 3.7 |
| IFN-9 | 3.6 | 3.6 | 3.7 | 3.7 |
| IFN-10 | 3.6 | 3.7 | 3.7 | 3.6 |
| IFN-11 | 3.5 | 3.6 | 3.5 | 3.6 |

TABLE DEP-17

Osmolality (OSM/kg)

| IFN-1 | 0.348 |
|---|---|
| IFN-2 | 0.345 |
| IFN-3 | 0.345 |
| IFN-4 | 0.346 |
| IFN-5 | 0.354 |
| IFN-6 | 0.358 |
| IFN-7 | 0.399 |
| IFN-8 | 0.354 |
| IFN-9 | 0.369 |

TABLE DEP-17-continued

Osmolality (OSM/kg)

| IFN-10 | 0.366 |
|---|---|
| IFN-11 | 0.361 |

The osmolality of the formulations tested is appropriate.

Based on the results of the formulation development, the following HSA-free formulation was selected:

44 or 88 mcg/ml Interferon beta-1a in sodium acetate buffer pH 3.5 containing 54.6 mg/ml mannitol, 1 mg/ml Poloxamer 188

0.12 mg/ml L-Methionine.

1.3.2 Overages

No overages were applied.

1.3.3 Physicochemical and Biological Properties

These characteristics have been considered in the formulation development studies, as described above.

1.4 Manufacturing Process Development 1.4.1 Development of the Manufacturing Process The current manufacturing process was adapted to the preparation of the lab-scale batches of the new formulation: the drug substance was directly compounded with the ingredients; then a double filtration was performed in order to mimic the industrial scale process which foresees an aseptic filtration followed by an in-line filtration before syringe filling. The syringes were then manually filled with the final sterile solution.

Both the filtration steps and the syringe filling were performed under laminar flow.

A description of each step of the process is given hereafter.

1.4.2 Preliminary Calculations

Amount of Interferon beta-1a drug substance D(mg) required to obtain a 44 mcg/ml solution:

$$D(mg) = 44 \text{ mcg/ml} \times 90 \text{ ml} = 3960 \text{ mcg} = 3.96 \text{ mg}$$

Volume of Interferon beta-1a drug substance B(ml) corresponding to the amount D(mg):

$$B(ml) = 3.96 \text{ mg: bulk titre (mg/ml)}$$

Volume of excipient solution V(ml) required to obtain 90 ml of the a 44 mcg/ml solution:

$$V(ml) = 90 \text{ ml} - B(ml)^*$$

*(d≅1 g/ml)

1.4.3 Preparation of Sodium Hydroxide 1 M Solution

A solution of 1 M sodium hydroxide was prepared in WFI.

1.4.4 Preparation of 0.01 M Sodium Acetate Buffer pH 3.5

An appropriate quantity of glacial acetic acid was added to WFI and the pH was adjusted to 3.5±0.2 using 1 M NaOH or 50% diluted acetic acid. The solution was completed to final volume using WFI.

1.4.5 Preparation of the Excipient Solution The calculated amount of excipients (mannitol, Tween 20 or Poloxamer 188, L-Methionine) was weighed and dissolved in the required amount of 0.01 M sodium acetate buffer pH 3.5; the pH is then checked and adjusted, if needed, to 3.5±0.2 with 1 M NaOH or 50% diluted acetic acid; the solution is then completed to final weight with 0.01 M sodium acetate buffer.

1.4.6 Compounding of the Drug Substance Solution

The required amount B(g) of Interferon beta-1a drug substance is added to the required amount of excipient solution V(g) and gently stirred to homogeneity.

1.4.7 1$^{st}$ Filtration of the Drug Substance Solution

The compounded solution is then filtered through a 0.2 μm nylon membrane (Ultipor $N_{66}$ 0.2 μm, ø 2.5 cm, Pall), mounted into a stainless steel holder, under nitrogen pressure (1 bar max) and collected into a glass beaker.

1.4.8 2$^{nd}$ Filtration of the Drug Substance Solution

The solution from the previous filtration is then filtered again through a new 0.2 μm nylon membrane under the same conditions.

1.4.9 Filling of Syringes 1 ml glass syringes were aseptically filled with 0.5 ml of the final solution.

1.4.10 Temperature During the Process

During the whole process the temperature is maintained as close as possible to refrigerated conditions, by using refrigerated W.F.I. and by storing the excipient solution and the compounded solutions at 2-8° C.

Example 2

Liquid Multi-dose HSA-free Interferon Beta-1a Formulation in Cartridges Suitable for an Auto-injector The need to develop a multi-dose product in cartridges arose during the development of a new HSA-free formulation which aimed at the elimination of HSA from the currently marketed product in syringes. The multi-dose formulation would increase patient convenience by allowing self-administration by an auto-injector.

The most commonly used bacteriostatic agents (0.3% m-cresol, 0.5% phenol and 0.9% benzyl alcohol) were initially studied in combination with the active substance and compared to the mono-dose formula in syringe selected in the frame of the mono-dose development (44 or 88 mcg/ml Interferon beta-1a, 54.6 mg/ml mannitol, 1 mg/ml Poloxamer 188, 0.12 mg/ml L-methionine in 10 mM sodium acetate buffer at pH 3.5); the following was observed:

the inclusion of each of the bacteriostatic agents, at the concentrations commonly used to prevent microbial contamination, determined an increase in the oxidised forms and promoted a dramatic increase in aggregation;

0.3% m-cresol and the combination of 0.5% phenol with 0.1% Poloxamer 188 determined a dramatic increase in aggregation.

Based on the information obtained during the pre-formulation, the formulation development focused initially on benzyl alcohol and phenol (without Poloxamer 188) as well as on additional bacteriostatic agents (chlorobutanol, phenylethanol); EDTA was also investigated in combination with benzyl alcohol: oxidation and aggregation of the active drug were the main degradation pathways observed; the reduction of the amount of benzyl alcohol in the formulation was shown to increase the shelf-life of the product.

All the other preservative agents investigated during this phase did not result in a significant improvement of the stability of the product.

At the end of the formulation development the following candidate multi-dose formulations were identified:

Formulation B—264 mcg Interferon beta-1a, 163.8 mg mannitol, 3 mg Poloxamer 188, 0.36 mg L-methionine, 6 mg benzyl alcohol in 3 ml of 10 mM sodium acetate buffer pH 3.5

Formulation A—264 mcg Interferon beta-1a, 163.8 mg mannitol, 3 mg Poloxamer 188, 0.36 mg L-methionine in 2.7 ml of 11 mM sodium acetate buffer pH 3.5 to be mixed with 0.3 ml of 3% benzyl alcohol in WFI thus obtaining the final multi-dose formulation.

Three lab-scale batches were manufactured for each candidate formulation and tested by stability indicating methods up to 6 months: no significant degradation occurred for both candidate formulations upon storage at 2-8° C.; the main degradation occurring upon accelerated conditions (25° C.) is oxidation. At the end of the study, two candidate multi-dose formulations were identified with a comparable stability profile:

Formulation B is a ready-to-use multi-dose formulation containing 0.2% benzyl alcohol;

Formulation A is multi-dose formulation containing 0.3% benzyl alcohol which is obtained after mixing the content of 2 cartridges (one containing the active principle and the excipients and one containing the required amount of benzyl alcohol to reach the final presentation).

2.1 Aim of the Study

The aim of this study was to develop a multi-dose HSA-free formulation of Interferon beta-1a at 264 mcg in 3 ml cartridges to allow administration by an auto-injector.

2.2 Experimental Part 2.2.1 Materials

Interferon-beta-1a (Serono S. A.)
Mannitol DAB, Ph Eur, BP, USP, FCC, E421 (Merck)
Glacial acetic acid 100% GR (Merck)
Sodium hydroxide pellets GR (Merck)
Poloxamer 188 (Lutrol F 68 DAC, USP/NF, BASF)
L-Methionine for biochemistry (Merck)
m-Cresol for synthesis (Merck)
Phenol for synthesis (Merck)
Benzyl alcohol Ph Eur, BP, NF (Merck)
Chlorobutanol (Aldrich)
Phenylethanol (Sigma)
Sodium methylparaben BP, USP/NF (Formenti)
Sodium propylparaben BP, USP/NF (Formenti)
EDTA disodium salt (Fluka)
1,2-Propanediol extrapure DAB, Ph Eur, BP, USP (Merck)
Acetonitrile (Merck)
Trifluoroacetic acid (Baker)
Heptafluorobutirric acid (Pierce)

2.2.2 Equipment

HPLC systems (Waters)
Millennium 32 Software (Waters)
Osmometer (Osmomat 030-D, Gonotec)
pH meter (mod. 654, Metrohm)
Calibrated pipettes (Gilson)
Ultipor N66 0.2 μm nylon membranes, FTKNF, ø 4.7 cm (Pall)
Ultipor N66 0.2 μm nylon membranes, NR14225, ø14.2 cm (Pall)
Stainless steel holders, ø 0 4.7 cm and ø 10 cm (Sartorius)
Stainless steel tank (Sartorius)
C4 Column 5 μm (0.46×25 cm) (Baker)
C4 Column, Supelcosil LC-304 5 μm (0.46×25 cm) (Supelco)
TSK Column, G2000SWXL (0.46×25 cm) (TosoHaas)

2.3 Pre-Formulation Study

The most commonly used bacteriostatic agents (0.3% m-cresol, 0.5% phenol and 0.9% benzyl alcohol) were initially studied in combination with the active substance and different excipient mixtures in the final container (3 ml cartridges): acetate buffer, acetate buffer/mannitol, acetate buffer/mannitol/L-Met/(Poloxamer 188. The compatibility of the active substance in the different environments was investigated in terms of oxidation (by RP-HPLC) and aggregation (by SE-HPLC) upon storage at 40° C. A summary of the formulations investigated during the different steps of this preliminary phase is given in Tab. 1.

The effect of the inclusion of each bacteriostatic agent was compared to the mono-dose formula (reference) selected in the frame of a mono-dose development in syringe (44 or 88 mcg/ml Interferon beta-1a, 54.6 mg/ml mannitol, 1 mg/ml Poloxamer 188, 0.12 mg/ml L-methionine in 10 mM sodium acetate buffer at pH 3.5).

2.4. Formulation Development

Based on the information obtained during the pre-formulation, the formulation development focused initially on benzyl alcohol and phenol; additional preservative agents (chlorobutanol, phenylethanol) and EDTA combined to benzyl alcohol were also investigated. A comparative formulation (MS-3), corresponding to the new HSA-free formulation of Interferon beta-1a mono-dose, was also prepared in cartridges and used as reference.

The composition (in mg/ml) of the formulations manufactured during this phase is reported in Tabs 2 to 5:

TABLE 1

Compositions of Interferon beta-1a multi-dose formulations (pre-formulation)

| Formulation | Composition |
|---|---|
| Reference | Ace/Man/Plu/Met1 |
| E | Ace/CR |
| F | Ace/PH |
| G | Ace/BA |
| H | Ace |
| I | Ace/Man/CR |
| J | Ace/Man/PH |
| K | Ace/Man/BA |
| L | Ace/Man |
| M | Ace/Man/PH |
| N | Ace/Man/Met1/PH |
| O | Ace/Man/Met2/PH |
| P | Ace/Man/Plu/PH |
| Q | Ace/Man/Plu/Met1/PH |
| R | Ace/Man/Plu/Met2/PH |
| S | Ace/Man/BA |
| T | Ace/Man/Met1/BA |
| U | Ace/Man/Met2/BA |
| V | Ace/Man/Plu/BA |
| W | Ace/Man/Plu/Met1/BA |
| X | Ace/Man/Plu/Met2/BA |

Ace = 10 mM sodium acetate buffer pH 3.5;
Man = 54.6 mg/ml;
Plu = 1 mg/ml Poloxamer 188;
Met1 = 0.12 mg/ml L-methionine;
Met2 = 0.24 mg/ml L-methionine;
CR = 3 mg/ml m-cresol;
PH = 5 mg/ml phenol;
BA = 9 mg/ml benzyl alcohol

TABLE 2

Interferon beta-1a multi-dose formulations containing benzyl alcohol (composition in mg/ml)

| # | IFN | Mannitol | Poloxamer 188 | L-Met | Benzyl alcohol | Acetate buffer |
|---|---|---|---|---|---|---|
| MS-3 (ref.) | 0.088 | 54.6 | 1 | 0.12 | — | q.s. to 1 ml |
| MS-13 | 0.088 | 54.6 | 1 | 0.12 | 1.5 | q.s. to 1 ml |
| MS-14 | 0.088 | 54.6 | — | 0.12 | 1.5 | q.s. to 1 ml |
| MS-15 | 0.088 | 54.6 | 1 | 0.12 | 3 | q.s. to 1 ml |
| MS-16 | 0.088 | 54.6 | — | 0.12 | 3 | q.s. to 1 ml |
| MS-17 | 0.088 | 54.6 | 1 | 0.12 | 4.5 | q.s. to 1 ml |
| MS-18 | 0.088 | 54.6 | — | 0.12 | 4.5 | q.s. to 1 ml |
| MS-1 | 0.088 | 54.6 | 1 | 0.12 | 9 | q.s. to 1 ml |
| MS-2 | 0.088 | 54.6 | — | 0.12 | 9 | q.s. to 1 ml |

TABLE 3

Interferon beta-1a multi-dose formulations containing phenol (in mg/ml)

| # | IFN | Mannitol | Propylene glycol | Phenol | Acetate buffer |
|---|---|---|---|---|---|
| MS-4 | 0.088 | 54.6 | — | 5 | q.s. to 1 ml |
| MS-5 | 0.088 | 54.6 | 100 | 5 | q.s. to 1 ml |

TABLE 4

Interferon beta-1a multi-dose formulations containing chlorobutanol and phenylethanol (in mg/ml)

| # | IFN | Mannitol | Poloxamer 188 | L-Met | Chlorobutanol | Phenylethanol | Acetate buffer |
|---|---|---|---|---|---|---|---|
| MS-35 | 0.088 | 54.6 | 1 | 0.12 | 1 | — | q.s. to 1 ml |
| MS-34 | 0.088 | 54.6 | 1 | 0.12 | — | 1 | q.s. to 1 ml |
| MS-34b | 0.088 | 54.6 | 1 | 0.12 | — | 1 | q.s. to 1 ml |

TABLE 5

Interferon beta-1a multi-dose formulations containing EDTA (in mg/ml)

| # | IFN | Mannitol | L-Met | Poloxamer 188 | EDTA | Benzyl alcohol | Acetate buffer |
|---|---|---|---|---|---|---|---|
| MS-32 | 0.088 | 54.6 | 0.12 | 1 | 1 | 2 | q.s. to 1 ml |
| MS-33 | 0.088 | 54.6 | — | 1 | 1 | 2 | q.s. to 1 ml |
| MS-36 | 0.088 | 54.6 | 0.12 | 1 | 0.5 | 1 | q.s. to 1 ml |

At the end of the formulation development the following candidate multi-dose formulations were identified:

Formulation B—264 mcg Interferon beta-1a in 3 ml acetate buffer at pH 3.5 containing 54.6 mg/ml mannitol, 1 mg/ml Poloxamer 188, 0.12 mg/ml L-Methionine and 2 mg/ml benzyl alcohol (0.2% benzyl alcohol)

Formulation A—264 mcg Interferon beta-1a in 2.7 ml acetate buffer at pH 3.5 containing 54.6 mg/ml mannitol, 1 mg/ml Poloxamer 188 and 0.12 mg/ml L-Methionine to be mixed with 0.3 ml of 3% benzyl alcohol in WFI thus obtaining the final multi-dose formulation (0.3% benzyl alcohol)

2.5 Preservative efficacy test

Multi-dose formulations containing different concentrations of benzyl alcohol (0.2% to 0.9%) were screened for the preservative efficacy test according to EP and USP Pharmacopeia.

Preliminary tests were performed by selecting as indicators Staphylococcus aureus, Aspergillus niger and Candida albicans: the evidence that the acidic pH of the formulation has itself a bacteriostatic effect on bacteria (Staphylococcus aureus) and the fact that some strains of Candida albicans are reported to survive even at low pH values (pH around 2) led to the selection of Candida albicans as the critical indicator for the test The acceptance criteria for the preservative efficacy test described in both EP and USP Pharmacopeia were applied.

2.6 Candidate Formulations 2.6.1 Formulation A

Three lab-scale batches of about 140 cartridges/batch were manufactured; the formula is given in Tab. 6:

TABLE 6

Composition of Interferon beta-1a multi-dose Formulation A

| IFNβ-1a | Mannitol | Poloxamer 188 | L-Methionine | 11 mM Sodium acetate pH 3.5 |
|---|---|---|---|---|
| 97.8 mcg | 60.7 mg | 1.11 mg | 0.13 mg | q.s. to 1.0 ml |

The active ingredient was compounded with the excipients solution and then filtered through a 0.22 μm nylon membrane; cartridges were filled with 2.7 ml final solution. Samples were taken before, after filtration and after filling to monitor losses of the active principle during the process.

Samples were stored and tested for stability at 2-8° C. (6 months), 25±2° C. (3 months) and 40±2° C. (1 month).

Six lab-scale batches of 3% benzyl alcohol in WFI were manufactured to be mixed with the cartridges containing the active ingredient; the composition of the batches is given in Tab. 7:

TABLE 7

Composition of 3% benzyl alcohol in WFI

| Benzyl alcohol | WFI |
|---|---|
| 30 mg | q.s. to 1.0 ml |

The required amount of benzyl alcohol was added to WFI and then filtered through a 0.22 μm Durapore membrane; cartridges were then filled with 0.5 ml and terminally sterilised by autoclaving.

Samples were stored at 25±2° C. and tested for benzyl alcohol content and pH up to 1 month.

2.6.2 Formulation B

Three lab-scale batches of about 500 cartridges/batch were manufactured; the composition is given in Tab. 8:

TABLE 8

Composition of Interferon beta-1a multi-dose Formulation B

| IFNβ-1° | Mannitol | Poloxamer 188 | L-Methionine | Benzyl alcohol | 10 mM Sodium acetate pH 3.5 |
|---|---|---|---|---|---|
| 88 mcg | 54.6 mg | 1 mg | 0.12 mg | 2 mg | q.s. to 1.0 ml |

The active ingredient was compounded with the excipients solution and then filtered through a 0.22 μm nylon membrane; cartridges were filled with 3 ml final solution. Samples were taken before, after filtration and after filling to monitor losses of the active principle during the process.

Samples were stored and tested for stability at 2-8° C. (6 months), 25±2° C. (6 months) and 40±2° C. (3 weeks).

2.6.3 Preservative Efficacy Test

Both candidate formulations were tested for preservative efficacy according to EP and USP Pharmacopeia.

2.7 Analytical Tests and Methods

The analytical tests and methods described below have been used to monitor the stability of the lab-scale formulations:

pH (potentiometric measurement)

Protein Quantitation Assay (RP-HPLC)

The quantification of the protein is performed on a C4, Wide-Pore Butyl 5 μm column (Baker); the wavelength is set at 214 nm and the elution is performed at 1 mL/min using the following mobile phase and gradient:

A=Water/trifluoroacetic Acid 0.1%–B=Acetonitrile/trifluoroacetic Acid 0.1%–C=acetonitrile Gradient:

| 0 min | 70% A | 30% B | 0% C |
|---|---|---|---|
| 5.0 min | 70% A | 30% B | 0% C |
| 6.0 min | 58% A | 42% B | 0% C |
| 15.0 min | 57% A | 43% B | 0% C |
| 30.0 min | 46% A | 54% B | 0% C |
| 35.0 min | 45% A | 55% B | 0% C |
| 40.0 min | 40% A | 60% B | 0% C |
| 40.1 min | 20% A | 80% B | 0% C |
| 45.0 min | 20% A | 80% B | 0% C |
| 45.1 min | 0% A | 0% B | 100% C |
| 50.0 min | 0% A | 0% B | 100% C |
| 50.1 min | 70% A | 30% B | 0% C |
| 65.0 min | 70% A | 30% B | 0% C |

Runtime = 65 min

Samples are analysed by injecting 100 μL of a samples as it is (44 mcg/mL samples) or upon dilution (1:1) in an equivalent placebo for samples at 88 mcg/mL.

The quantification of the samples is performed versus a standard curve in the range 0.0125 mg/mL-0.2 mg/mL prepared by a reference standard material.

Oxidised Forms (RP-HPLC)

The quantification of the oxidised forms is performed on a C4, Supelcosil LC-304 column (Supelco) thermostated at 40° C.; the wavelength is set at 208 nm and the elution is performed at 1 mL/min using the following mobile phase and gradient:

A=water 60%/acetonitrile 40%/Heptafluorobutirric acid 0.14%–B=water 20%/Acetonitrile 80%/Heptafluorobutirric acid 0.14%–C=water 20%/Acetonitrile 80%/Trifluroacetic acid 0.1%
Gradient:

| 0'  | 70% A | 30% B  | 0% C   |         |
|-----|-------|--------|--------|---------|
| 5'  | 70% A | 30% B  | 0% C   |         |
| 58' | 62% A | 38% B  | 0% C   | Curve 6 |
| 63' | 0% A  | 100% B | 0% C   | Curve 1 |
| 68' | 0% A  | 0% B   | 100% C | Curve 1 |
| 69' | 70% A | 30% B  | 0% C   | Curve 6 |

Runtime: 96 minutes (70 min + 26 min equilibration)

Samples are analysed as it is by injecting 200 μL (88 mcg/mL samples) or 400 μL (44 mcg/mL samples).

Total Aggregates (SE-HPLC)

The detection of the total aggregates content is performed on a TSK G2000SWXL column (TosoHaas); the elution is performed in isocratic mode at 0.5 mL/min using acetonitrile: water (30:70)+0.2% trifluoracetic acid; the wavelength is set at 214 nm. The runtime is 20 min.

Samples are analysed as it is by injecting 100 μL (88 mcg/mL samples) or 200 μL (44 mcg/mL samples).

Biological Activity (in Vitro Bioassay)

The biological activity is measured by an antiviral assay based on the IFN-β induced protection of cells (WISH cells-human amniotic tissue) against the cytopathic effect of a virus (Vesicular Stomatitis Virus).

Osmolality (Cryoscopic Measurement)

The osmolality determination is performed by a cryoscopic measurement based on the freezing-point depression observed for the solution tested.

Benzyl Alcohol Assay (GC)

The GC method to detect benzyl alcohol uses the single point calibration approach, using as reference the benzyl alcohol as supplied by Merck. In addition an internal standard (phenylethyl alcohol) is used to normalize the peak areas of both test samples, control sample solution and of the standard solution. The method is carried out onto a 6 feet×2 mm ID steel column with 10% Carbowax 20M on supelcoport 80/100 mesh. The detector is a FID (flame ionization detector). The results are expressed as mg of benzyl alcohol per mL.

2.7.1 Results
2.7.1.1 Pre-Formulation

The levels of oxidised forms and total aggregates detected upon stressed conditions (40° C.) are shown in Tables 9 and 10:

Tab. 9:% Oxidised forms in Interferon beta-1a multi-dose formulations upon storage at 40° C. (by RP-HPLC)

| Formulation | Composition     | T = 0 | 3 days at 40° C. | 6 days at 40° C. |
|-------------|-----------------|-------|------------------|------------------|
| Reference   | Ace/Man/Plu/Met1 | 3.0  | —                | 4.2              |
| E           | Ace/CR          | 2.8   | 2.7              | —                |
| F           | Ace/PH          | 2.6   | 3.5              | —                |
| G           | Ace/BA          | 2.6   | 6.3              | —                |
| H           | Ace             | 3.6   | 2.7              | —                |
| I           | Ace/Man/CR      | 2.3   | 3.0              | —                |
| J           | Ace/Man/PH      | 3.6   | 2.5              | —                |
| K           | Ace/Man/BA      | 4.0   | 4.7              | —                |
| L           | Ace/Man         | 2.9   | 2.3              | —                |
| M           | Ace/Man/PH      | 2.9   | —                | 6.3              |
| N           | Ace/Man/Met1/PH | 2.7   | —                | 5.3              |
| O           | Ace/Man/Met2/PH | 2.5   | —                | 4.9              |
| P           | Ace/Man/Plu/PH  | 2.3   | —                | 6.8              |
| Q           | Ace/Man/Plu/Met1/PH | 2.2 | —              | 7.2              |
| R           | Ace/Man/Plu/Met2/PH | 2.1 | —              | 4.2              |
| S           | Ace/Man/BA      | 2.6   | —                | 5.0              |
| T           | Ace/Man/Met1/BA | 2.7   | —                | 5.0              |
| U           | Ace/Man/Met2/BA | 2.5   | —                | 4.8              |
| V           | Ace/Man/Plu/BA  | 2.5   | —                | 5.0              |
| W           | Ace/Man/Plu/Met1/BA | 2.6 | —              | 5.0              |
| X           | Ace/Man/Plu/Met2/BA | 3.0 | —              | 6.2              |

Ace = 10 mM sodium acetate buffer pH 3.5;
Man = 54.6 mg/ml;
Plu = 1 mg/ml Poloxamer 188;
Met1 = 0.12 mg/ml L-methionine;
Met2 = 0.24 mg/ml L-methionine;
CR = 3 mg/ml m-cresol;
PH = 5 mg/ml phenol;
BA = 9 mg/ml benzyl alcohol

TABLE 10

% Total aggregates in Interferon beta-1a multi-dose formulations upon storage at 40° C. (by RP-HPLC)

| Formulation | Composition         | T = 0 | 3 days at 40° C. | 6 days at 40° C. |
|-------------|---------------------|-------|------------------|------------------|
| Reference   | Ace/Man/Plu/Met1    | 3.2   | —                | 3.2              |
| E           | Ace/CR              | 1.8   | 9.4              | 8.5              |
| F           | Ace/PH              | 2.2   | 39.8             | 9.4              |
| G           | Ace/BA              | 2.0   | 4.7              | 7.2              |
| H           | Ace                 | 2.8   | 2.5              | 1.7              |
| I           | Ace/Man/CR          | 2.4   | 15.6             | 20.1             |
| J           | Ace/Man/PH          | 2.0   | 2.3              | 2.1              |
| K           | Ace/Man/BA          | 2.3   | 3.6              | 4.5              |
| L           | Ace/Man             | 3.0   | 3.2              | 2.3              |
| M           | Ace/Man/PH          | 2.2   | —                | 4.4              |
| N           | Ace/Man/Met1/PH     | 2.2   | —                | 5.8              |
| O           | Ace/Man/Met2/PH     | 2.3   | —                | 8.8              |
| P           | Ace/Man/Plu/PH      | 2.2   | —                | 40.3             |
| Q           | Ace/Man/Plu/Met1/PH | 2.3   | —                | 46.3             |
| R           | Ace/Man/Plu/Met2/PH | 2.3   | —                | 35.9             |
| S           | Ace/Man/BA          | 2.5   | —                | 3.4              |
| T           | Ace/Man/Met1/BA     | 2.6   | —                | 5.4              |
| U           | Ace/Man/Met2/BA     | 1.4   | —                | 3.0              |
| V           | Ace/Man/Plu/BA      | 2.9   | —                | 4.8              |
| W           | Ace/Man/Plu/Met1/BA | 2.9   | —                | 5.8              |
| X           | Ace/Man/Plu/Met2/BA | 1.6   | —                | 5.8              |

Ace = 10 mM sodium acetate buffer pH 3.5;
Man = 54.6 mg/ml;
Plu = 1 mg/ml Poloxamer 188;
Met1 = 0.12 mg/ml L-methionine;
Met2 = 0.24 mg/ml L-methionine;
CR = 3 mg/ml m-cresol;
PH = 5 mg/ml phenol;
BA = 9 mg/ml benzyl alcohol The inclusion of each of the bacteriostatic agents, at the concentrations commonly used to prevent microbial contamination, determined an increase in the oxidised forms and promoted a dramatic increase in aggregation compared to the mono-dose formulation (Reference).

The combination of 0.5% phenol and 0.1% Poloxamer 188 negatively affected the stability of the product since about 40% aggregation occurred (formulations P-Q-R). 0.3% m-cresol was excluded for further development since negatively affecting the stability of the product due to an increase in aggregation (formulation 1).

2.7.1.2 Formulation Development

All the stability data (raw data) are collected in the section Tables; linear regression analysis was used to evaluate the data.

2.7.1.2.1 Formulations Containing Benzyl Alcohol

Figure 2:
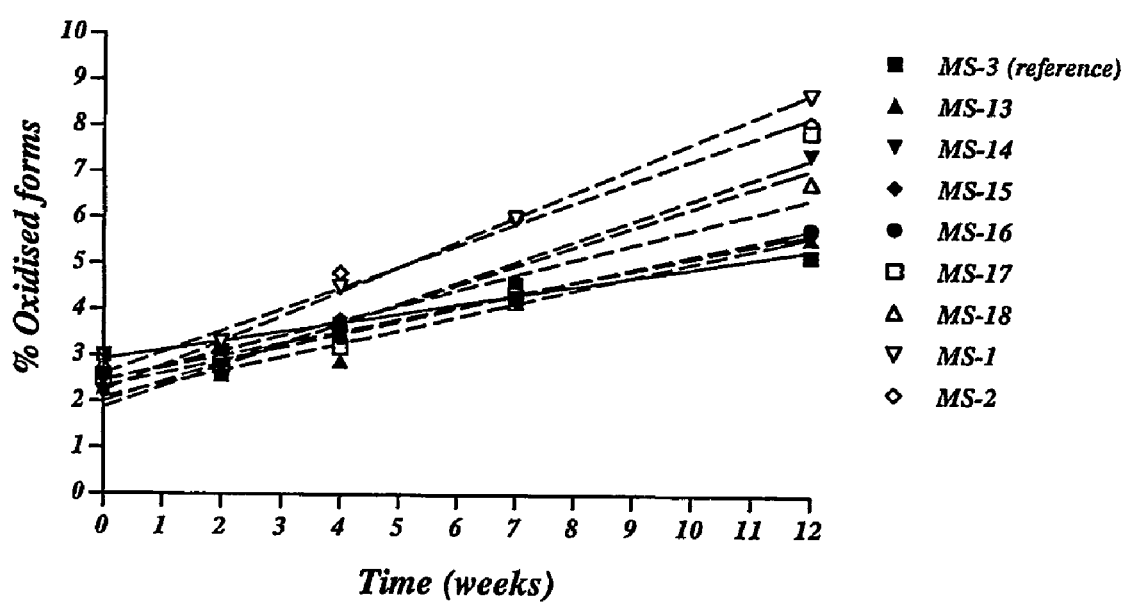
FIG. 2: it reports the percentage of oxidised forms, which are present in Interferon beta-1a multi-dose formulations having different concentrations of benzyl alcohol after storage at 25° C.
Figure 3:
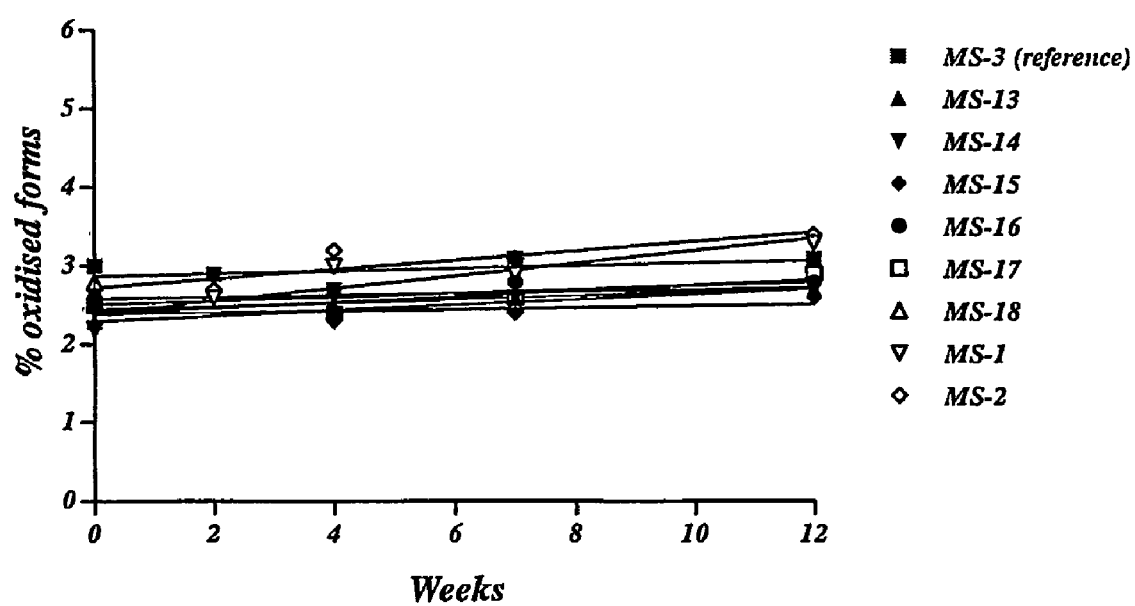
FIG. 3: it shows the percentage of oxidised forms, which are present in Interferon beta-1a multi-dose formulations having different concentrations of benzyl alcohol after storage at 2-8° C.

A high concentration of benzyl alcohol (0.9%) negatively affected the stability of the product both in terms of oxidised forms and aggregates content, as shown in FIGS. 1 to 6:

upon stressed conditions (40° C.), the increase in oxidation is higher for the formulations containing 0.9% benzyl alcohol (MS-1 and MS-2), as shown in FIG. 1;

upon accelerated conditions (25° C.), the increase in oxidation is higher for all the formulations containing benzyl alcohol compared to the formulation without benzyl alcohol (MS-3, reference), as shown in FIG. 2;

upon long-term storage (2-8° C.), higher oxidation rates were observed for the formulations containing 0.9% benzyl alcohol (MS-1 and MS-2); comparable degradation rates were detected for formulations containing benzyl alcohol below 0.45% (FIG. 3).

Figure 4:
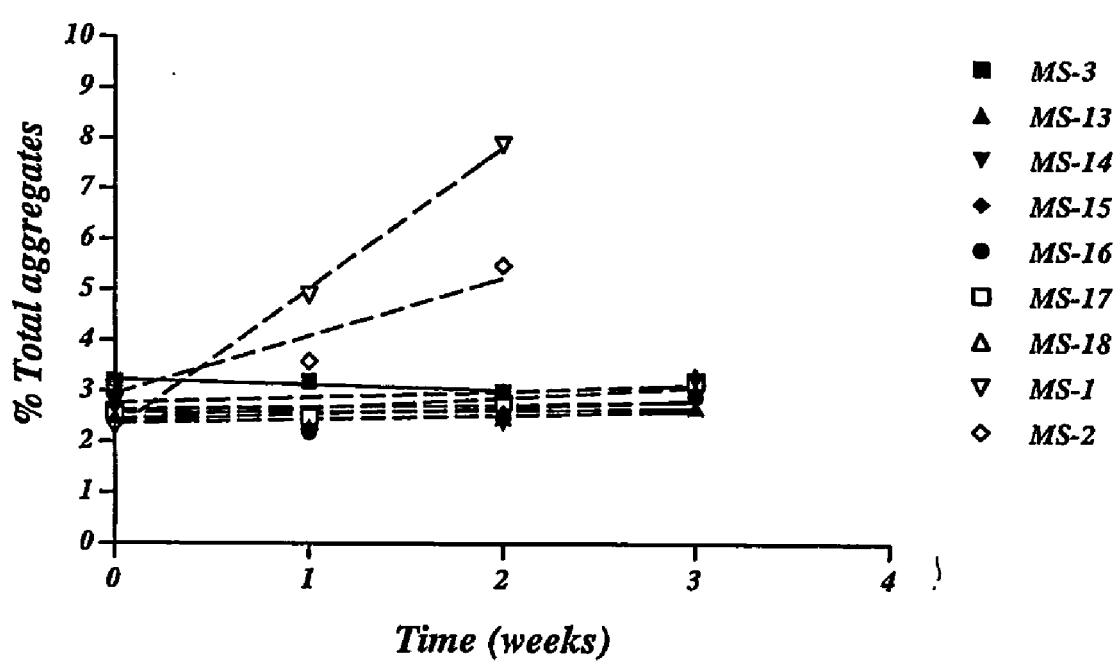
FIG. 4: it reports the percentage of total aggregates, which are present in Interferon beta-1a multi-dose formulations having different concentrations of benzyl alcohol after storage at 40° C.
Figure 5:
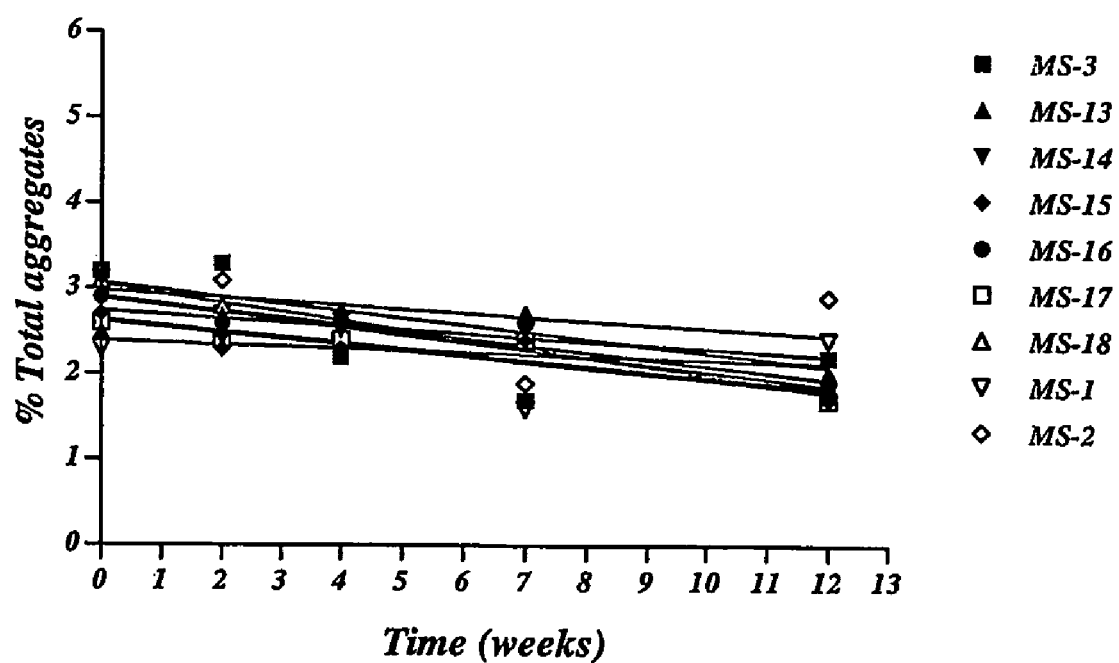
FIG. 5: it reports the percentage of total aggregates, which are present in Interferon beta-1a multi-dose formulations having different concentrations of benzyl alcohol after storage at 25° C.
Figure 6:
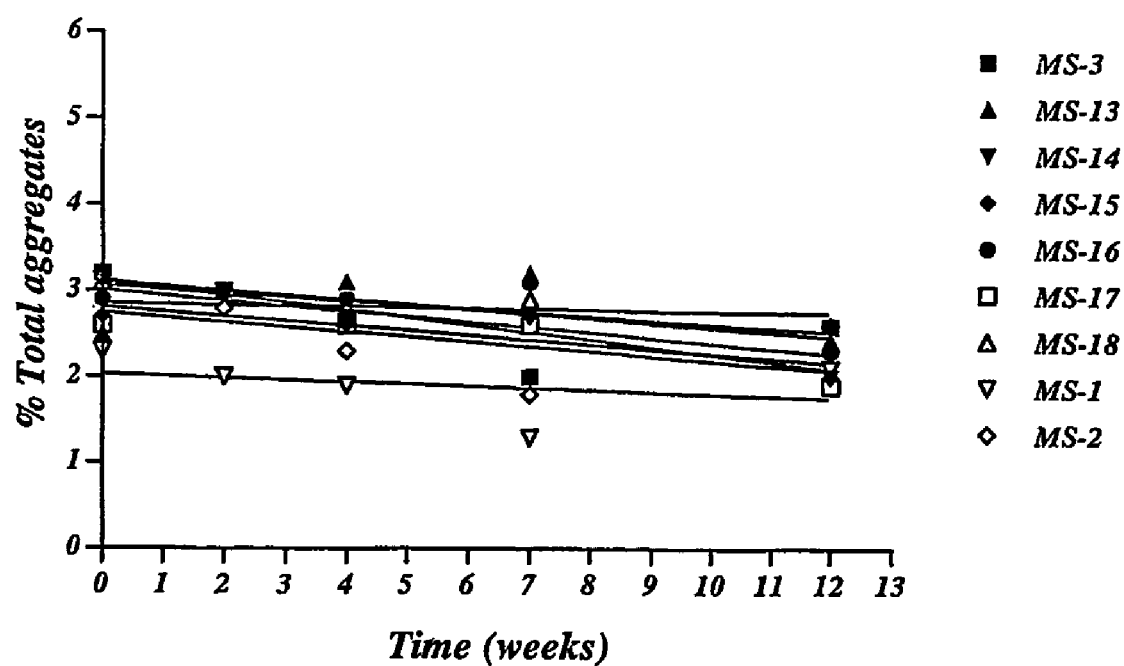
FIG. 6: it reports the percentage of total aggregates, which are present in Interferon beta-1a multi-dose formulations having different concentrations of benzyl alcohol after storage at 2-8° C.

As for the level of aggregates the following was observed:

upon stressed conditions (40° C.), the increase in aggregation was observed for the formulations containing 0.9% benzyl alcohol (MS-1 and MS-2), as shown in FIG. 4;

upon accelerated and long term conditions (25° C. and 2-8° C.), no increase in aggregation was observed for all the formulations, as shown in FIGS. 5 and 6;

A decrease in bioactivity was observed for formulations with 0.9% benzyl alcohol (MS-1 and MS-2) at 40° C.; this is not observed for the same samples stored at 25° C. and 2-8° C. No decrease in titre was observed upon storage at all temperatures.

No pH shift occurred upon storage at all temperatures.

2.7.1.2.2 Formulations Containing Alternative Bacteriostatic Agents (Phenol, Chlorobutanol, Phenylethanol)

Figure 7:
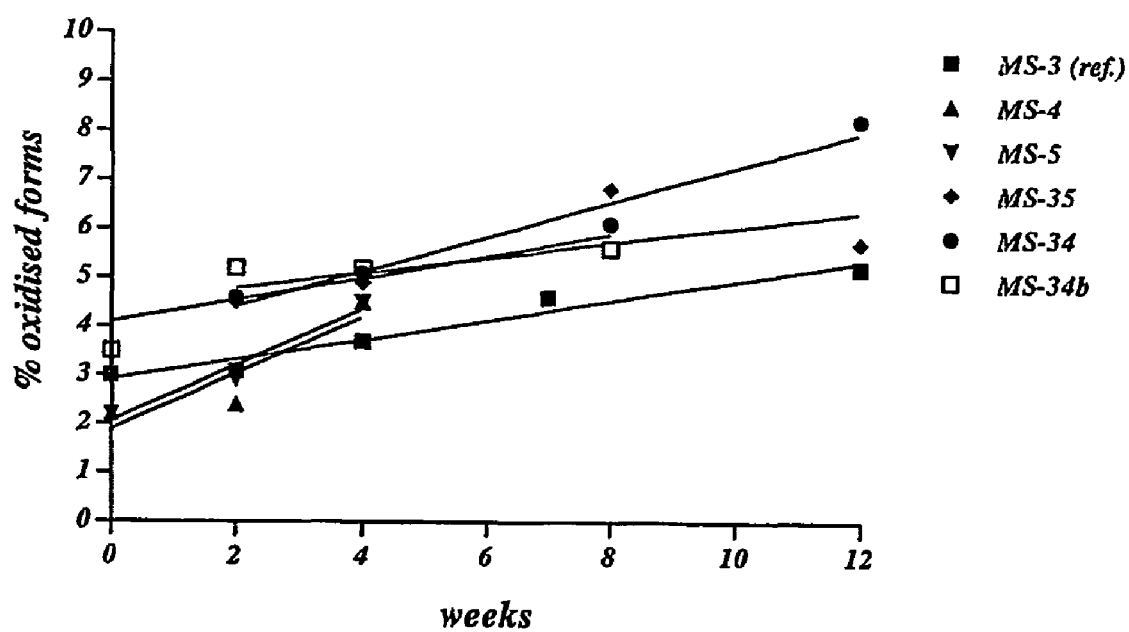
FIG. 7: it shows the percentage of oxidised forms, which are present in Interferon beta-1a multi-dose formulations containing alternative bacteriostatic agents after storage at 25° C.
Figure 8:
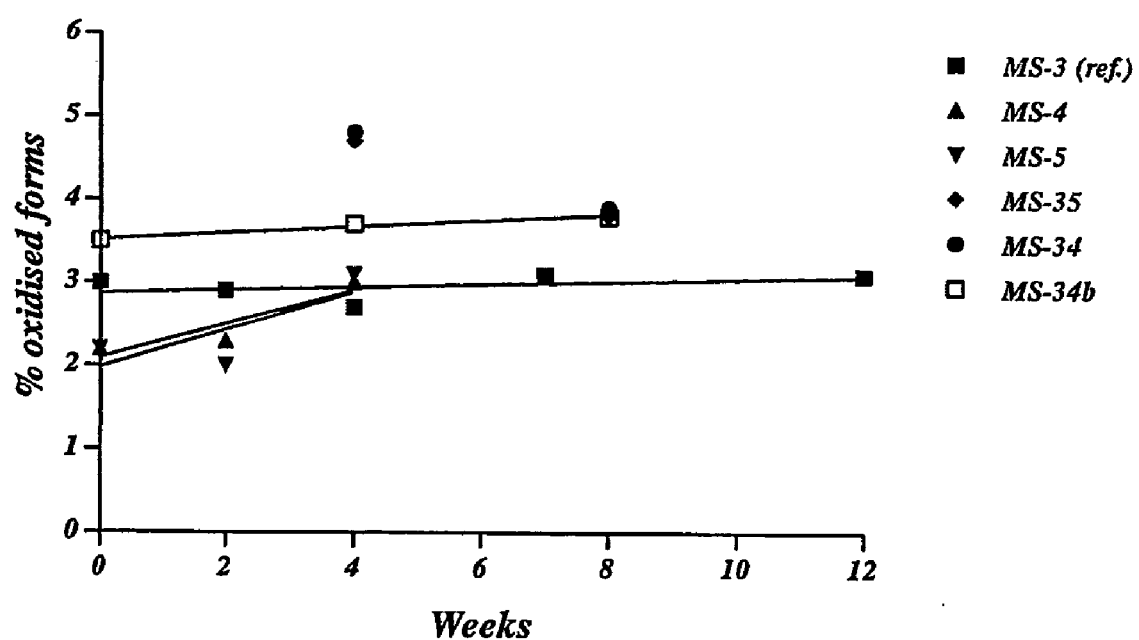
FIG. 8: it reports the percentage of oxidised forms, which are present in Interferon beta-1a multi-dose formulations containing alternative bacteriostatic agents after storage at 2-8° C.
Figure 9:
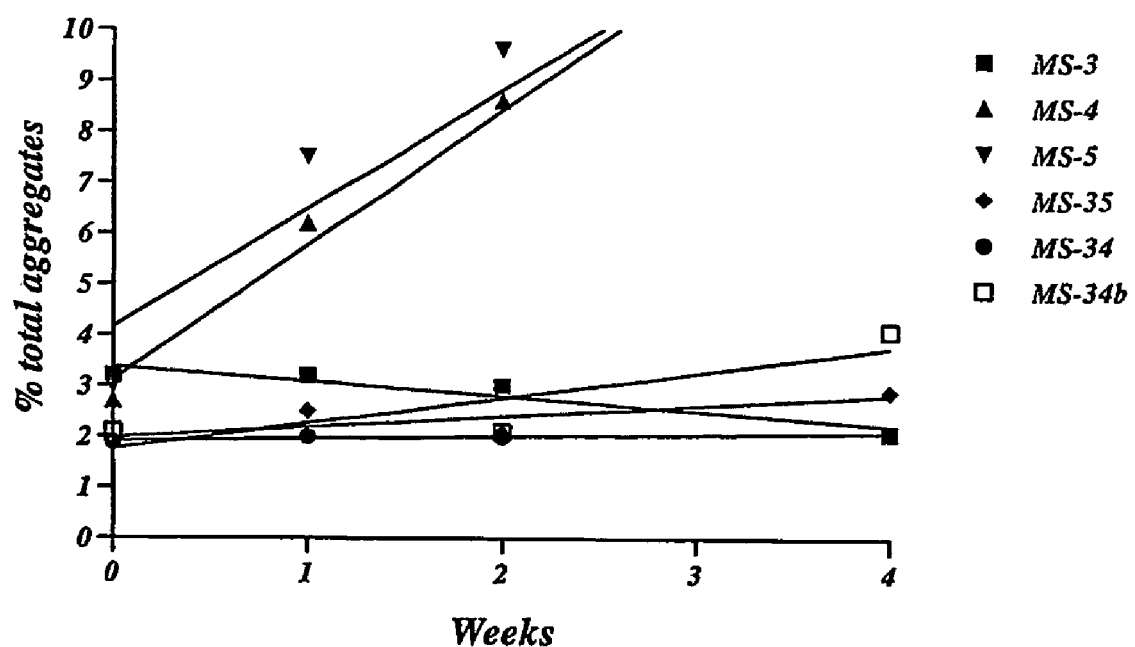
FIG. 9: it reports the percentage of total aggregates, which are present in Interferon beta-1a multi-dose formulations containing alternative bacteriostatic agents.

Phenol (MS-4 and MS-5) negatively affected the stability of the product in terms of oxidised forms while chlorobutanol (MS-35) and phenylethanol (MS-34 and MS-34b) showed a stability comparable to the reference solution (MS-3, without bacteriostatic), as shown in FIGS. 7 and 8:

As for the level of total aggregates, a dramatic increase in aggregation was observed upon stressed conditions (40° C.) for the formulations containing phenol (MS-4 and MS-5) as shown in FIG. 9; no increase in aggregation occurred at lower temperatures (25° C. and 2-8° C.).

2.7.1.2.3 Formulations Containing EDTA

Figure 10:
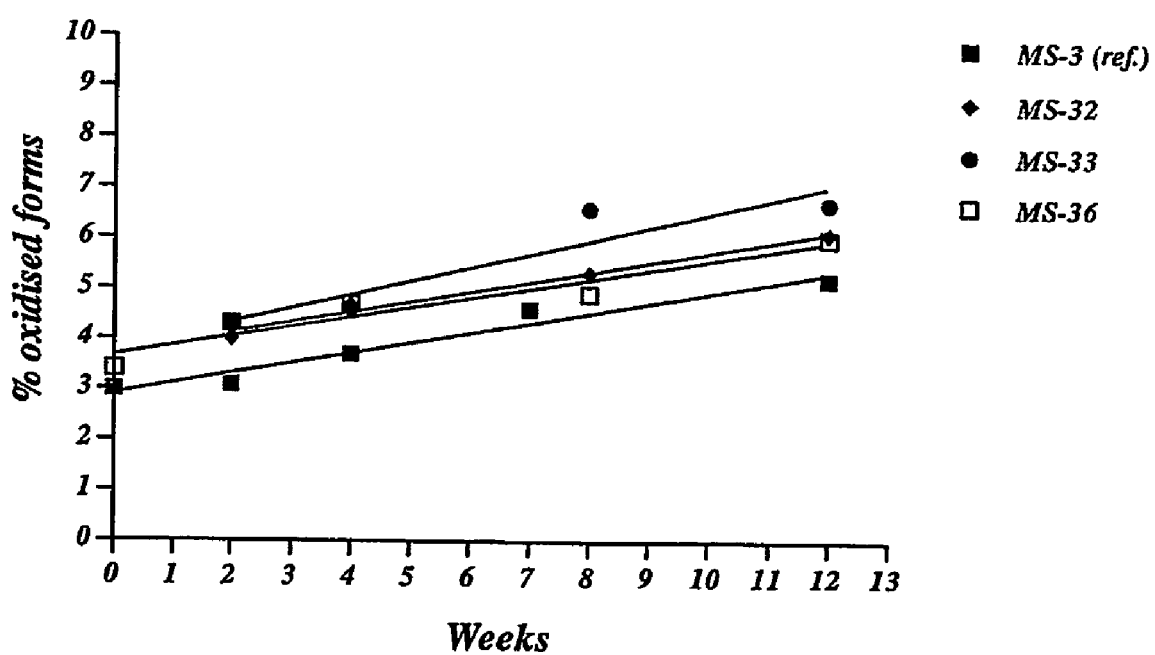
FIG. 10: it shows the percentage of oxidised forms, which are present in Interferon beta-1a multi-dose formulations containing EDTA after storage at 25° C.
Figure 11:
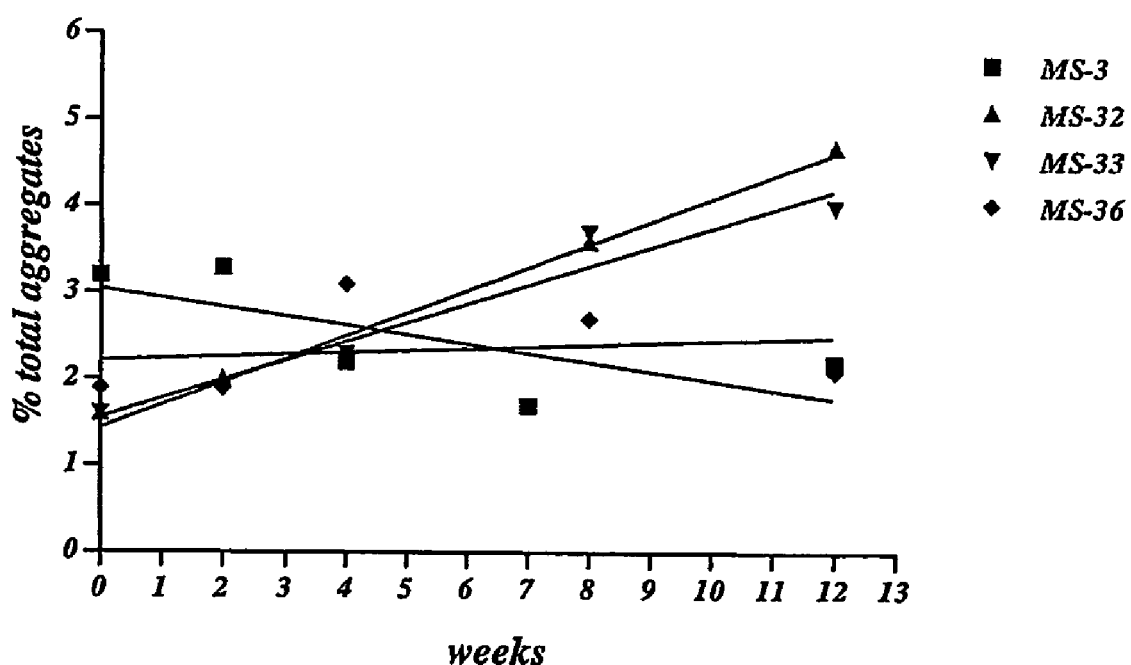
FIG. 11: it shows the percentage of total aggregates, which are present in Interferon beta-1a multi-dose formulations containing EDTA after storage at 25° C.

The addition of EDTA to formulations containing 0.1%-0.2% benzyl alcohol (MS-32, MS-33, MS-36) did not lower the level of oxidation (FIG. 10); an increase in the level of aggregates was observed upon accelerated conditions for formulations containing 0.1% EDTA and 0.2% benzyl alcohol (MS-32, MS-33) (FIG. 11); comparable degradation were observed at 2-8° C.:

2.7.1.2.4 Preservative Efficacy Results

The results of the screening study showed that the USP and EP Pharmacopoeia criteria are satisfied at least for concentrations of benzyl alcohol which are equal to or higher than 0.3% (for Candida albicans).

2.8 Candidate Formulations

The evaluation of all the data was performed in the following way: a linear regression analysis was performed for each batch, followed by covariance analysis (P-value >0.25) to assess batch-to-batch variability, no formal statistical analysis was performed when no variability was observed upon storage.

2.8.1 Candidate A
2.8.1.1 Recovery During Manufacturing

The recovery of Interferon beta-1a in the in-process samples (before and after filtration, finished product) collected during the manufacturing of the candidate A are summarized in Tab. 11: no significant loss of the active ingredient was recorded.

TABLE 11

| % Interferon beta-1a recovery during manufacturing of candidate A | | | |
|---|---|---|---|
| | RT-01 | RT-02 | RT-03 |
| After 1st filtration | 98.6 | 99.7 | 98.0 |
| After 2nd filtration | 98.3 | 98.5 | 103.8 |
| Finished product in cartridge | 98.4 | 97.5 | 100.7 |

2.8.1.2 Stability of Active Drug

A common slope and intercept were calculated for the level of oxidised forms in the three batches stored at different temperatures; the results of the statistical analysis are shown in Tab. 12:

TABLE 12

Results of statistical analysis for Interferon beta-1a multi-dose candidate A (oxidised forms)

| 2-8° C. | | 25° C. | | 40° C. | |
|---|---|---|---|---|---|
| Pooled slope (%/week) | Pooled intercept (%) | Pooled slope (%/week) | Pooled intercept (%) | Pooled slope (%/week) | Pooled intercept (%) |
| 0.063 | 2.73 | 0.322 | 2.67 | 2.206 | 2.51 |

No significant variability was observed for the level of total aggregates and the assay; therefore, no formal statistical analysis was performed. The different level in aggregates for the three batches is due to the different level in the bulks used for the manufacturing.

2.8.2 Candidate B
2.8.2.1 Recovery During Manufacturing

The recovery of Interferon beta-1a in the in-process samples (before and after filtration, finished product) collected during the manufacturing of the candidate B are summarized in Tab. 15: no significant losses of the active ingredient were recorded.

TABLE 15

| % Interferon beta-1a recovery during manufacturing of candidate B | | | |
|---|---|---|---|
| | MS-01 | MS-02 | MS-03 |
| After 1st filtration | 100.7 | 116.5 | 97.38 |
| After 2nd filtration | 101.2 | 114.9 | 98.82 |
| Finished product in cartridge | 100.6 | 112.0 | 95.76 |

2.8.2.2 Stability of Active Drug

The statistical analysis performed on the level of oxidised forms showed the following:

a common slope and intercept were calculated for the 3 batches at 40° C.: the pooled slope equals 1.42%/week and the pooled intercept equals 2.72%;

no common slope could be calculated for the 3 batches at 25° C. (P-value=0.095); therefore, the worst case approach (batch MS-03) was used: an increase of 1.17% in the oxidised forms was observed after 1 month storage (0.27%/week);

no common slope could be calculated for the 3 batches at 2-8° C. (P-value=0.016); therefore, the worst case approach (batch MS-03) was used: an increase of 0.2% in the oxidised forms was observed after 1 month storage (0.047%/week).

No significant variability was observed from the stability data for the level of total aggregates and the assay; therefore, no formal statistical analysis was performed.

No decrease in bioactivity was observed upon storage, even upon stressed conditions (40° C.).

2.9 Conclusions

At the end of the study, two candidate multi-dose formulations were identified with a comparable stability profile:

Candidate Formulation B is a ready-to-use multi-dose formulation containing 0.2% benzyl alcohol;

Candidate Formulation A is multi-dose formulation containing 0.3% benzyl alcohol which is obtained after mixing the content of 2 cartridges (one containing the active principle and the excipients and one containing the required amount of benzyl alcohol to reach the final presentation).

These candidates solutions were also tested at a higher pH (4.5±0.2), and no significant changes in the stability profile have been shown. The Applicant has now found that this slightly higher pH of the IFN formulations increases local tolerability of subcutaneous injections. Therefore the above 2 candidate solutions at a pH of 4.5 or 4.7 could offer further advantages in terms of patient compliance.

Example 3

Manufacturing Method for the
Multi-Dose—Candidate Formulation A

First the sodium hydroxide 1 N solution was prepared by dissolving 20 g of sodium hydroxide pellets in 500 g of W.F.I.

Then the 0.011 M sodium acetate buffer at ph 3.5±0.2 was prepared by adding 1.32 g of glacial acetic acid to about 1,800 g of W.F.I. The pH of the solution to pH 3.5±0.2 was adjusted with 1 N NaOH. Then the solution is taken to final weight of 2000 g. The pH is then again adjusted to 3.5±2 with 1 N NaOH or 50% diluted acetic acid. The solution is then taken to final weight of 2000 g.

The final solution was prepared as follows.

The calculated amount of excipients was weighed and dissolved in the required amount of 11 mM sodium acetate buffer at pH 3.5±0.2, and the pH of the solution checked and adjusted (if needed); then the required amount of r-h Interferon-beta-1a (recombinantly produced from CHO cells) is added; the final weight is reached by adding 11 mM sodium acetate buffer at pH 3.5±0.2.

1 ml of this final solution was sampled to be tested by quantitative RP HPLC (sample BF=Before $1^{st}$ Filtration).

The final solution was then filtered through a 0.2 µm membrane mounted into a stainless steel holder and the solution collected into a glass beaker.

1 ml of this final solution was sampled to be tested by quantitative RP HPLC.

The final solution filtered as described at the previous point was filtered through a $2^{nd}$ 0.2 µm membrane mounted into a stainless steel holder.

1 ml of this final solution was sampled to be tested by quantitative RP HPLC.

3 ml glass cartridges were filled with 2.7 ml of the final solution and stoppered.

This solution is ready to be mixed with a cartridge containing the 3% benzyl alcohol solution in WFI.

Example 4

Manufacturing Method for Multi-Dose—Candidate
Formulation B

First the sodium hydroxide 1 N solution was prepared by dissolving 20 g of sodium hydroxide pellets in 500 g of W.F.I.

Then the 0.011 M sodium acetate buffer at pH 3.5±0.2 was prepared by adding 1.32 g of glacial acetic acid to about 1800 g of W.F.I. The pH of the solution was adjusted to ph 3.5±0.2 with 1 N NaOH. Then the solution was taken to final weight of 2000 g. The pH was then again adjusted to 3.5±0.2 with 1 N NaOH or 50% diluted acetic acid. The solution was then taken to final weight of 2000 g.

The final solution was prepared as follows.

The calculated amount of excipients was weighed and dissolved in the required amount of 10 mM sodium acetate buffer at pH 3.5±0.2, and the pH of the solution checked and adjusted (if needed); then the required amount of r-h Interferon-beta-1a (recombinantly produced from CHO cells) was added; the final weight was reached by adding 10 mM sodium acetate buffer at pH 3.5±0.2.

1 ml of this final solution is sampled to be tested by quantitative RP HPLC.

The final solution is then filtered through a 0.2 µm membrane mounted into a stainless steel holder and the solution collected into a glass beaker.

1 ml of this final solution is sampled to be tested by quantitative RP HPLC.

The final solution filtered as described at the previous point is filtered through a $2^{nd}$ 0.2 ml membrane mounted into a stainless steel holder.

1 ml of this final solution is sampled to be tested by quantitative RP HPLC.

3 ml glass cartridges are filled with 3 ml of the final solution and stoppered.

REFERENCES

1. Study Group. The Lancet 1998; 352, 1498-1504.
2. Clegg and Bryant, Exp. Opin. Parmacother 2001; 2(4): 623-3639.
3. Derynk R. et al., Nature 1980; 285, 542-547.
4. Familletti, P. C., Rubinstein, S., and Pestka, S. 1981 "A Convenient and Rapid Cytopathic Effect Inhibition Assay for Interferon," in Methods in Enzymology, Vol. 78 (S. Pestka, ed.), Academic Press, New York, 387-394;
5. Hultgren C, Milich D R, Weiland O, Sallberg M. (1998). The antiviral compound ribavirin modulates the T helper (Th) 1/Th2 subset balance in hepatitis B and C virus-specific immune responses. J Gen Virol 1998; 79:2381-2391.
6. McCormick J B, King I J, Webb P A, Scribner C L, Craven R B, Johnson K M, Elliott L H, Belmont-Williams R. Lassa fever. Effective therapy with ribavirin. N Engl J Med. 1986 Jan. 2; 314(1):20-6.
7. Mark D. F. et al., Proc. Natl. Acad. Sci. U.S.A., 81 (18) 5662-5666 (1984).
8. Pestka, S. (1986) "Interferon Standards and General Abbreviations, in Methods in Enzymology (S. Pestka, ed.), Academic Press, New York 119, 14-23.
9. Rubinstein, S., Familletti, P. C., and Pestka, S. Convenient Assay for Interferons. J. Virol 1981; 37, 755-758.
10. Shepard H. M. et al., Nature 1981; 294, 563-565.

The invention claimed is:

1. A stabilized and preserved aqueous pharmaceutical composition free of human serum albumin, comprising:
   interferon-β1a in an amount of about 10 μg/ml to about 800 μg/ml;
   acetate buffer present in an amount to maintain the pH of the composition within plus or minus 0.5 units of a specified pH, where the specified pH is about 3.0 to about 5.0;
   poloxamer 188 surfactant in an amount of about 0.01 mg/ml to about 10 mg/ml;
   methionine in an amount of about 0.01 to about 5.0 mg/ml;
   benzyl alcohol in an amount of about 0.1% to about 2.0%; and
   mannitol in an amount of 0.5 mg/ml to about 500 mg/ml.

2. The composition of claim 1, wherein said acetate buffer is present at a concentration of about 5 mM to 500 mM.

3. The composition of claim 1, wherein said acetate buffer is present at a concentration of about 10 mM.

4. The composition of claim 1 in which the interferon-β1a is present in an amount of about 44 μg/ml.

5. The composition of claim 4, wherein said acetate buffer is present at a concentration of about 5 mM to 500 mM.

6. The composition of claim 4, wherein said acetate buffer is present at a concentration of about 10 mM.

7. The composition of claim 1 in which the interferon-β1a is present in an amount of about 88 μg/ml.

8. The composition of claim 7, wherein said acetate buffer is present at a concentration of about 5 mM to 500 mM.

9. The composition of claim 7, wherein said acetate buffer is present at a concentration of about 10 mM.

10. A stabilized and preserved aqueous pharmaceutical composition free of human serum albumin, consisting essentially of:
    interferon-β1a in an amount of about 10 μg/ml to about 800 μg/ml;
    acetate buffer present in an amount to maintain the pH of the composition within plus or minus 0.5 units of a specified pH, where the specified pH is about 3.0 to about 5.0;
    poloxamer 188 surfactant in an amount of about 0.01 mg/ml to about 10 mg/ml;
    methionine in an amount of about 0.01 to about 5.0 mg/ml;
    benzyl alcohol in an amount of about 0.1% to about 2.0%;
    mannitol in an amount of 0.5 mg/ml to about 500 mg/ml; and
    water.

11. The composition of claim 10 in which the interferon-β1a is present in an amount of about 44 μg/ml.

12. The composition of claim 10 in which the interferon-β1a is present in an amount of about 88 μg/ml.

13. A stabilized and preserved aqueous pharmaceutical composition free of human serum albumin, consisting of:
    interferon-β1a in an amount of about 10 μg/ml to about 800 μg/ml;
    acetate buffer present in an amount to maintain the pH of the composition within plus or minus 0.5 units of a specified pH, where the specified pH is about 3.0 to about 5.0;
    poloxamer 188 surfactant in an amount of about 0.01 mg/ml to about 10 mg/ml;
    methionine in an amount of about 0.01 to about 5.0 mg/ml;
    benzyl alcohol in an amount of about 0.1% to about 2.0%;
    mannitol in an amount of 0.5 mg/ml to about 500 mg/ml; and
    water.

14. The composition of claim 13 in which the interferon-β1a is present in an amount of about 44 μg/ml.

15. The composition of claim 13 in which the interferon-β1a is present in an amount of about 88 μg/ml.

* * * * *

SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: linker sequence

<400> SEQUENCE: 1

```
Glu Phe Gly Ala Gly Leu Val Leu Gly Gly Gln Phe Met
1               5                   10
```